US008703747B2

(12) United States Patent
Roques et al.

(10) Patent No.: US 8,703,747 B2
(45) Date of Patent: Apr. 22, 2014

(54) AMINOPHOSPHINIC DERIVATIVES THAT CAN BE USED IN THE TREATMENT OF PAIN

(75) Inventors: Bernard Roques, Paris (FR); Hervé Poras, Bailly (FR); Marie-Claude Fournie-Zaluski, Paris (FR)

(73) Assignee: Pharmaleads, Paris (FR)

( * ) Notice: Subject to any disclaimer, the term of this patent is extended or adjusted under 35 U.S.C. 154(b) by 331 days.

(21) Appl. No.: 13/055,096

(22) PCT Filed: Jul. 22, 2009

(86) PCT No.: PCT/EP2009/059394
§ 371 (c)(1),
(2), (4) Date: Jan. 20, 2011

(87) PCT Pub. No.: WO2010/010106
PCT Pub. Date: Jan. 28, 2010

(65) Prior Publication Data
US 2011/0124601 A1    May 26, 2011

(30) Foreign Application Priority Data

Jul. 23, 2008    (FR) ..................... 08 55015

(51) Int. Cl.
*A61K 31/66*    (2006.01)
*A01N 57/00*    (2006.01)
*A01N 57/18*    (2006.01)

(52) U.S. Cl.
USPC ............................ 514/121; 514/141; 514/119

(58) Field of Classification Search
USPC ......................... 514/121, 141, 119
See application file for complete search history.

(56) References Cited

U.S. PATENT DOCUMENTS

| 4,738,803 | A | 4/1988 | Roques et al. |
| 5,476,847 | A | 12/1995 | McKittrick et al. |
| 6,391,866 | B1 * | 5/2002 | Roques et al. ............... 514/119 |
| 6,518,260 | B1 * | 2/2003 | Fournie-Zaluski et al. ... 514/141 |
| 6,593,368 | B2 * | 7/2003 | Magnus-Miller et al. .... 514/561 |
| 2006/0111325 | A1 * | 5/2006 | Gallop ............................ 514/91 |
| 2011/0071218 | A1 * | 3/2011 | Fournie-Zaluski et al. ... 514/454 |

FOREIGN PATENT DOCUMENTS

| FR | 853092 | 4/1939 |
| FR | 2 518 088 | 6/1983 |
| FR | 2 605 004 A1 | 4/1988 |
| FR | 2 651 229 A1 | 3/1991 |
| FR | 2 755 135 A1 | 4/1998 |
| FR | 2 777 780 A1 | 10/1999 |
| FR | 2 892 413 A1 | 4/2007 |
| FR | 2 892 414 A1 | 4/2007 |
| WO | WO 97/00261 | 1/1997 |

OTHER PUBLICATIONS

Huixiong Chen, et al, Long Lasting Antinociceptive Properties of Enkephalin Degrading Enzyme (NEP and APN) Inhibitor Prodrugs, 44 J Med. Chem. 3523 (2001).*

Burger'S Medicinal Chemistry: Part I, The Basis of Medicinal Chemistry 336-37 (Manfred E. Wolff, ed., John Wiley & Sons, Inc. 1980) (1905).*

Alexander et al., "(Acyloxy)alkyl Carbamates as Novel Bioreversible Prodrugs for Amines: Increased Permeation through Biological Membranes," J. Med. Chem., 1988, pp. 318-322, vol. 31, No. 2.

Allen et al., "Ethyl Benzalmalonate," Organic Syntheses, Coll., 1955, p. 377, vol. 3; 1945, p. 42, vol. 25.

Baylis et al., "1-Aminoalkylphosphonous Acids. Part 1. Isosteres of the Protein Amino Acids," J. Chem. Soc. Perkin Trans., 1984, pp. 2845-2853.

Bennett et al., "A peripheral mononeuropathy in rat that produces disorders of pain sensation like those seen in man," Pain, 1988, pp. 87-107, vol. 33.

Bourgoin et al., "Effects of Kelatorphan and Other Peptidase Inhibitors on the in Vitro and in Vivo Release of Methionine-Enkephalin-Like Material from the Rat Spinal Cord," J Pharmacology and Experimental Therapeutics, 1986, pp. 360-366, vol. 238, No. 1.

Bras et al., "Met-Enkephalin is Preferentially Transported Into the Peripheral Processes of Primary Afferent Fibres in Both Control and HSV1-Driven Proenkephalin A Overexpressing Rats," Neuroscience, 2001, pp. 1073-1083, vol. 103, No. 4.

Chaplan et al., "Quantitative assessment of *Tactile allodynia* in the rat paw," J Neuroscience Methods, 1994, pp. 55-63, vol. 53.

Chen et al., "Long Lasting Antinociceptive Properties of Enkephalin Degrading Enzyme (NEP and APN) Inhibitor Prodrugs," J. Med. Chem., 2001, pp. 3523-3530, vol. 44, No. 21.

Chen et al., "Phosphinic Derivatives as New Dual Enkephalin-Degrading enzyme Inhibitors: Synthesis, Biological Properties, and Antinociceptive Activities," J. Med. Chem., 2000, pp. 1398-1408, vol. 43, No. 7.

(Continued)

*Primary Examiner* — Sean Basquill
(74) *Attorney, Agent, or Firm* — Foley & Lardner LLP

(57) ABSTRACT

The present invention relates to a compound of the following general formula (I): $R_1-NH-CH(R_2)-P(=O)(OR_3)-CH_2-C(R_4)(R_5)-CONH-CH(R_6)-COOR_7$ (I) or a pharmaceutically acceptable salt of the latter, an isomer or a mixture of isomers in any proportions, especially a mixture of enantiomers, and in particular a racemic mixture, for which $R_1$ represents a $-C(=O)-O-C(R^8)(R^9)-OC(=O)-R^{10}$ group; $R_2$ represents an optionally substituted hydrocarbon-based chain, an aryl or heteroaryl group or a methylene group substituted by a heterocycle; $R_3$ represents a hydrogen atom or a $-C(R^{12})(R^{13})-OC(=O)-R^{14}$ group; $R_4$ and $R_5$ form, together with the carbon that bears them, a saturated hydrocarbon-based ring or an optionally substituted piperidine ring or $R_4$ represents a hydrogen atom and $R_5$ represents a phenyl or a benzyl that is optionally substituted, a heteroaromatic ring or a methylene group substituted by a heterocycle; $R_6$ represents an optionally substituted hydrocarbon-based chain or a phenyl or a benzyl that is optionally substituted; and $R_7$ represents a hydrogen atom or a benzyl, alkyl, heteroaryl, alkylheteroaryl, $-CHMe-COOR^{18}$, $-CHR^{19}-OC(=O)OR^{20}$ and $-CHR^{19}-OC(=O)OR^{20}$ group. The present invention also relates to the use of these compounds as a medicinal product, and in particular for the treatment of pain, more advantageously neuropathic and neuroinflammatory pain, to their method of synthesis and also to the compositions containing them.

8 Claims, 3 Drawing Sheets

(56) References Cited

OTHER PUBLICATIONS

Figure 1:
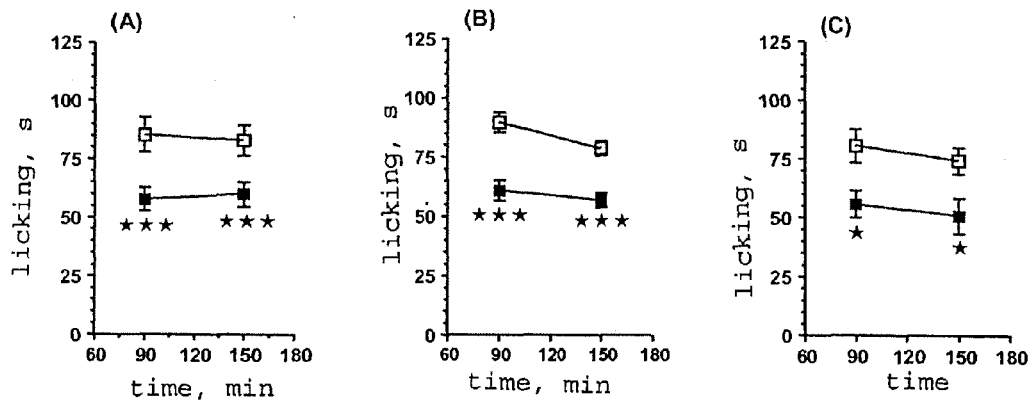

Fournié-Zaluski et al., "'Mixed Inhibitor—Prodrug' as a New Approach toward Systemically Active Inhibitors of Enkephalin-Degrading Enzymes," J. Med. Chem., 1992, pp. 2473-2481, vol. 35, No. 13.

Fournie-Zaluski et al., "Analgesic Effects of Kelatorphan, a New Highly Potent Inhibitor of Multiple Enkephalin Degrading Enzymes," European J Pharma., 1984, pp. 525-528, vol. 102.

Le Guen et al., "Pain management by a new series of dual inhibitors of enkephalin degrading enzymes: long lasting antinociceptive properties and potentiation by $CCK_2$ antagonist or methadone," Pain, 2003, pp. 139-148, vol. 104.

Hassan et al., "Inflammation of the Rat Paw Enhances Axonal Transport of Opioid Receptors in the Sciatic Nerve and Increases Their Density in the Inflamed Tissue," Neuroscience, 1993, pp. 185-195, vol. 55, No. 1.

Hecker et al., "Prodrugs of Phosphates and Phosphonates," J. Med. Chem., 2008, pp. 2328-2345, vol. 51, No. 8.

Hunskaar et al., "Formalin test in mice, a useful technique for evaluating mild analgesics," J Neuroscience Methods, 1985, pp. 69-76, vol. 14.

International Search Report, issued in PCT/EP2009/059394 on Sep. 24, 2009.

Jutkiewicz E.M., "RB101-mediated Protection of Endogenous Opioids: Potential Therapeutic Utility?," CNS Drug Reviews, 2007, pp. 192-205, vol. 13, No. 2.

Kayser et al., "Potent antinociceptive effects of Kelatorphan (a highly efficient inhibitor of multiple enkephalin-degrading enzymes) systemically administered in normal and arthritic rats," Brain Research, 1989, pp. 94-101, vol. 497.

Maldonado et al., "Comparison of selective and complete inhibitors of enkephalin-degrading enzymes of morphine withdrawal syndrome," European J Pharma., 1989, pp. 199-207, vol. 165.

Malmberg et al., "Partial sciatic nerve injury in the mouse as a model of neuropathic pain: behavioral and neuroanatomical correlates," Pain, 1998, pp. 215-222, vol. 76.

McKittrick, et al., "Design and Synthesis of Phsophinic Acids that Triply Inhibit Endothelin Converting enzyme, Angiotensin Converting enzyme and Neutral Endopeptidase 24.11," Bioorganic & Medicinal Chemistry Letters, 1996, pp. 1629-1634, vol. 6, No. 14.

Menéndez et al., "Initial thermal heat hypoalgesia and delayed hyperalgesia in a murine model of bone cancer pain," Brain Research, 2003, pp. 102-109, vol. 969.

Millan M.J., "The Induction of Pain: An Integrative Review," Progress in Neurobiology, 1999, pp. 1-164, vol. 57.

Milne et al., "Quaternary naloxone blocks morphine analgesia in spinal but not intact rats," Neuroscience Letters, 1990, pp. 259-264, vol. 114.

Noble et al., "Protection of endogenous enkephalin catabolism as natural approach to novel analgesic and antidepressant drugs," Expert Opin. Ther. Targets, 2007, pp. 145-159, vol. 11, No. 2.

Przewlocki et al., "Gene Expression and Localization of Opioid Peptidees in Immune Cells of Inflamed Tissue: Functional Role in Antinociception," Neuroscience, 1992, pp. 491-500, vol. 48, No. 2.

Ranoux et al., "Botulinum Toxin Type A Induces Direct Analgesic Effects in Chronic Neuropathic Pain," Ann. Neurol., 2008, pp. 274-283, vol. 64.

Rittner et al., "Pain control by CXCR2 ligands through $Ca^{2+}$-regulated release of opioid peptides from polymorphonuclear cells," The FASEB Journal, FJ Express Full-Length Article, Dec. 2006, pp. E2177-E2188, vol. 20.

Rittner et al., "Pain control by CXCR2 ligands through $Ca^{2+}$-regulated release of opioid peptides from polymorphonuclear cells," The FASEB Journal, FJ Express Summary, Dec. 2006, pp. 2627-2629, vol. 20.

Roques B.P., "Novel approaches to targeting neuropeptide systems," TiPS, Dec. 2000, pp. 475-483, vol. 21.

Roques et al., "Neutral Endopeptidase 24.11: Structure, Inhibition, and Experimental and Clinical Pharmacology," Pharmacological Reviews, 1993, pp. 87-146, vol. 45, No. 1.

Salzet et al., "Crosstalk between nervous and immune systems through the animal kingdom: focus on opioids," TINS, 2000, pp. 550-555, vol. 23, No. 11.

Schmidt et al., "Analgesic responses elicited by endogenous enkephalins (protected by mixed peptidase inhibitors) in a variety of morphine-sensitive noxious tests," European J Pharma., 1991, pp. 253-262, vol. 192.

Sun et al., "N-Acyloxymethyl Carbamate Linked Prodrugs of Pseudomycins Are Novel Antifungal Agents," Bioorganic & Medicinal Chemistry Letters, 2001, pp. 1875-1879, vol. 11.

Waksman et al., "Autoradiographic comparison of the distribution of the neutral endopeptidasae 'enkephalinase' and of μ and δ opioid receptors in rat brain," Proc. Natl. Acad. Sci. USA, Mar. 1986, pp. 1523-1527, vol. 83.

Waksman et al., "In Vitro and In Vivo Effects of Kelatorphan on Enkephalin Metabolism in Rodent Brain," European J Pharma., 1985, pp. 233-243, vol. 117.

Wu et al., "A-317491, a selective $P2X_3/P2X_{2/3}$ receptor antagonist, reverses inflammatory mechanical hyperalgesia through action at peripheral receptors in rats," European J Pharma., 2004, pp. 45-53, vol. 504.

Zhou et al., "NAAG Peptidase Inhibitors and Their Potential for Diagnosis and Therapy," Nature Reviews: Drug Discovery, Dec. 2005, pp. 1015-1026, vol. 4.

Cundy et al., "XP13512 [(±)-1-([(α-Isobutanoyloxyethoxy)carbonyl] aminomethyl)-1-cyclohexane Acetic Acid], A Novel Gabapentin Prodrug: I. Design, Synthesis, Enzymatic Conversion to Gabapentin, and Transport by Intestinal Solute Transportors," The Journal of Pharmacology and Experimental Therapeutics, vol. 311, No. 1, pp. 315-323, 2004.

Cundy et al., "XP13512 [(±)-1-([(α-Isobutanoyloxyethoxy)carbonyl] aminomethyl)-1-cyclohexane Acetic Acid], A Novel Gabapentin Prodrug: II. Improved Oral Bioavailability, Dose Proportionality, and Colonic Absorption Compared with Gabapentin in Rats and Monkeys," The Journal of Pharmacology and Experimental Therapeutics, vol. 311, No. 1, pp. 324-333, 2004.

Hayashida et al., "Gabapentin Activates Spinal Noradrenergic Activity in Rats and Humans and Reduces Hypersensitivity after Surgery," Anesthesiology, vol. 106, pp. 557-562, 2007.

Hayashida et al., "Gabapentin Acts within the Locus coeruleus to Alleviate Neuropathic Pain," vol. 109, pp. 1077-1084, 2008.

Lewanowitsch et al., "Naloxone and its quaternary derivative, naloxone methiodid, have differing affinities for μ, σ, and κ opioid receptors in mouse brain homogenates," Brain Research, vol. 964, pp. 302-305, 2003.

Campbell et al., eds., "Emerging Strategies for the Treatment of Neuropathic Pain," International Association for the Study of Pain, Table of Contents, 2006.

* cited by examiner

AMINOPHOSPHINIC DERIVATIVES THAT CAN BE USED IN THE TREATMENT OF PAIN

The present invention relates to aminophosphinic compounds, the method for the preparation thereof and the use thereof in the treatment of pain such as neuropathic, neuroinflammatory, postoperative pain or sharp pain caused by excessive nociception.

The perception, transmission and regulation of nociceptive influxes are dependent on a plurality of neurotransmitters, particularly enkephalins. Enkephalins (Met-enkephalin and Leu-enkephalin) are pentapeptides initially detected in the brain of mammals (Hugues Nature 1975, 258, 577). Enkephalins essentially bind with two receptor classes, μ and δ receptors (Lord et al. Nature 1977, 267, 495) which have different functions and sites (Waksman et al. Proc. Natl. Acad. Sci. 1986, 83, 152).

The anti-nociceptive properties of enkephalins have been demonstrated after intracerebroventricular administration of exogenous enkephalins (Belluzi Nature 1976, 260, 625). However, this response is very transient due to very rapid metabolisation of these peptides by enzyme activities. Synthetic enkephalin analogues, modified to render them resistant to enzyme degradation have displayed anti-nociceptive properties equal to those of morphine, but have also exhibited the same adverse side effects as morphine.

Furthermore, it is known that the enkephalins (Tyr-Gly-Gly-Phe-Met and Tyr-Gly-Gly-Phe-Leu) are physiologically inactivated by two zinc metallopeptidases, neprilysin (EP 3.4.24.11, NEP) that cleaves the $Gly^3$-$Phe^4$ bond (Malfroy et al. Nature 1978, 276, 523) and aminopeptidase N (EC 3.4.11.2, APN) that cleaves the $Tyr^1$-$Gly^2$ bond of these peptides (Waksman et al. Eur. J. Pharmacol. 1985, 117, 233; Rogues et al. Pharmacological Reviews 1993, 45, 87-146).

The inhibition of these two enzyme activities, by protecting endogenous enkephalins completely from the enzyme degradation thereof (Bourgoin et al. J. Pharm. Exp. Ther. 1986, 238, 360), displays the pharmacological, particularly analgesic and antidepressant, activities of these neuropeptides (Rogues Trends Pharmacol. Sci. 2000, 21, 475; Jutkiewicz CNS Drugs Reviews 2007, 13, 192-206).

Recent research has demonstrated that the enkephalinergic system, consisting of enkephalins, NEP and APN inactivation enzymes and opioid receptors, was present on nocioceptors, i.e. on the extremely fine endings of the sensory nerves transmitting pain influxes (M. J. Millan Prog. in Neurobiology, 57, 1999, 1-164). In this way:

i) the preproenkephalin gene is expressed in the dorsal glands of the spinal nerves, and transported to the periphery on the nociceptors (Antunes-Bras J et al. Neuroscience 2001, 103, 1073-1083), ii) enkephalins are expressed in large quantities in immune cells attracted to damaged tissue (Przewlocki R et al. Neuroscience 1992, 48(2), 491-500) and released from these cells to the lesion site (Rittner H L et al. FASEB J. 2006, 20, 2627-2629), iii) opioid receptors are present on the peripheral endings (Hassan AHS et al. Neuroscience 1993, 55, 185-195), iv) finally the activity of the two NEP and APN peptidases is increased in the leukocytes recruited by inflammation (Salzet M et al. Trends in Neuroscience 2000, 23, 550-555).

Composite inhibitors of both enzyme activities, described in the prior art, are pro-drugs that can be classified into two major families.

The first family consists of amino acid derivatives associating, via a disulphide bridge, a powerful NEP inhibitor and a powerful APN inhibitor (FR 651 229, J. Med. Chem. 1992, 35, 2473). These molecules display an excellent intravenous (iv) anti-nociceptive activity. A new generation of more soluble molecules has made it possible to obtain compounds having a satisfactory oral activity (FR 2 892 413, FR 2 892 414 and FR 08/53092).

The second family comprises compounds jointly inhibiting APN and NEP. They are either hydroxamate function compounds (FR 2 518 088 and FR 2 605 004) or aminophosphinic compounds (FR 2 755 135 and FR 2 777 780).

The hydroxamate compounds, described in these documents, exhibit an excellent in vitro and in vivo activity after intracerebroventricular administration. This was particularly demonstrated in the following publications (Eur. J. Pharmacol. 1984, 102, 525-528; Eur. J. Pharmacol. 1989, 165, 199-207; Eur. J. Pharmacol. 1991, 192, 253-262). A significant activity was also observed after iv administration in an arthritic rat model (Brain Research 1989, 497, 94-101).

The aminophosphinic compounds described in the applications FR 2 755 135 and FR 2 777 780 have on the terminal nitrogen atom either a free amine function or an imine function. However, it was observed by the inventors that, under physiological conditions, compounds having such an imine function do not inhibit the activity of the two peptidases NEP and APN. The inventors discovered that, to ensure activity, it is important that the pro-drug regenerates a free amine function, which is not possible in the presence of an imine, under physiological conditions.

In the compounds described in the application FR 2 755 135, the phosphinic acid function is left free or is protected by a protective group which is an alkyl or a benzyl. However, it was then described that the activity decreases when the phosphinic acid function is not protected (Hecker S. J. and Erion M. D. J. Med. Chem. 2008, 51, 2328-2345).

In the compounds described in the application FR 2 777 780, the phosphinic acid function is protected by a protective group which is:

either a —CH(X)—O—C(O)—Y group, where X,Y=alkyl or phenyl;

or an S-acylthioethyl (SATE) ester group having the formula —$CH_2$—$CH_2$—S—CO—W, where W=alkyl or phenyl.

However, the SATE group cannot be used in human therapy due to the toxicity of the cyclic product (ethylene sulphide) generated by hydrolysis of the thioester in the human body (Hecker S. J. and Erion M. D. J. Med. Chem. 2008, 51, 2328-2345).

Furthermore, the inventors observed, for the first time, that the joint presence of a —CH(X)—O—C(O)—Y group, protecting the phosphinic acid function, and a free amine function gives rise to the formation of an inactive transfer product (formation of an amide —N—C(O)—Y not suitable for hydrolysis; see example 13).

However, in the case of the aminophosphinic derivatives described in the application FR 2 777 780, a satisfactory anti-nociceptive activity with a long period of action was demonstrated on animal nociception models after iv or ip (intraperitoneal) administration when the molecules under study were solubilised in a mixture of oil, ethanol and water (J. Med. Chem. 2000, 43, 1398-1408; J. Med. Chem. 2001, 44, 3523-3530; Pain 2003, 104, 139-148). However, none of these molecules was sufficiently soluble in a solute suitable for administration in humans, and no significant anti-nociceptive activity was detected after oral administration.

One of the aims of the invention is thus to provide stable novel aminophosphinic compounds, capable of jointly inhibiting with a long period of action (i.e. at least 2 hours) both enzyme activities (neprilysin and aminopeptidase N) responsible for enkephalin degradation and thus amplifying the pharmacological properties of said peptides significantly after oral administration or after placing in solution in a solute compatible with administration to humans.

In this aim, the primary amine function of the aminophosphinic inhibitors was substituted by physiologically acceptable temporary protection groups, the carboxylic acid function were optionally esterified and the phosphinic acid function was left free or was substituted by physiologically acceptable temporary protection groups. These protections gave rise to very stable molecules having a very satisfactory bioavailability.

A further aim of the invention is to provide novel compounds having the properties of morphine substances, particularly a strong analgesic effect on various types of pain (acute, inflammatory, neuropathic, etc.), beneficial effects on behaviour (reduction in emotional component of pain) along with peripheral effects (antidiarrhoeal, antitussive, etc.) without having the major drawbacks thereof (tolerance, physical and psychological dependence, respiratory depression, constipation, nausea, vomiting, sedation, etc.).

A further aim of the invention is to provide associations between the compounds of the present invention and compounds known for the antinociceptive properties thereof but having harmful side effects at high doses. These associations more specifically relate to morphine and the derivatives thereof, THC (tetrahydrocannabinol) and the derivatives thereof along with Gaba derivatives such as Gabapentin or Pregalbin. Indeed, high potentiation of the antinociceptive responses obtained by combining subactive doses of one of the compounds claimed in the present application and one of the analgesics mentioned above (morphine, THC, Gabapentin) was observed. Similarly, the compounds according to the invention may be advantageously associated, within the scope of the treatment of neuropathic pain, with one of the botulinum toxins, injected locally (Ranoux D. et al, 2008, Anal. Neurol., 64, 274-283). The compounds according to the invention may also be associated with purinergic receptor antagonists, particularly the P2X3 receptors, of which one of the selective antagonists is the compound A-317491 (Wu et al., 2004, Eur. J. Pharm., 504, 45-53).

The invention thus more specifically relates to compounds complying with the following general formula (I):

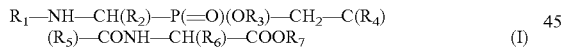

$$R_1\text{—NH—CH}(R_2)\text{—P}(\!=\!O)(OR_3)\text{—CH}_2\text{—C}(R_4) \\ (R_5)\text{—CONH—CH}(R_6)\text{—COOR}_7 \quad (I)$$

or a pharmaceutically acceptable salt thereof, where:

$R_1$ represents a group —C(=O)—O—C($R^8$)($R^9$)—OC(=O)—$R^{10}$, wherein
  $R^8$ and $R^9$ represent, independently of each other, a hydrogen atom or an alkyl, aryl, arylalkyl, cycloalkyl, cycloheteroalkyl, heteroalkyl, heteroaryl or heteroarylalkyl group; or
  ($R^8$ and $R^9$) form together, with the carbon bearing same, a saturated hydrocarbon cycle with 5 or 6 links;
  and $R^{10}$ represents an alkyl, aryl, arylalkyl, cycloalkyl, cycloheteroalkyl, heteroalkyl, heteroaryl or heteroarylalkyl group;

$R_2$ represents:
  a linear or branched saturated or unsaturated hydrocarbon chain, comprising 1 to 6 carbon atoms, and optionally substituted by
    a group $OR^{11}$, $SR^{11}$ or $SOR^{11}$, wherein $R^{11}$ represents a hydrogen atom, a benzyl group or a linear or branched saturated or unsaturated hydrocarbon chain, comprising 1 to 4 carbon atoms;
    an amino group; or
    a phenyl optionally substituted by one or a plurality of halogen atoms such as fluorine;
  an aryl or heteroaryl group, advantageously a phenyl, optionally substituted by one or a plurality of halogen atoms such as fluorine;
  a methylene group substituted by a saturated or aromatic heterocycle with 5 or 6 links, comprising one or a plurality of heteroatoms selected from sulphur and nitrogen, optionally oxidised in N-oxide or S-oxide form;

$R_3$ represents a hydrogen atom or a group having the formula —C($R^{12}$)($R^{13}$)—OC(=O)—$R^{14}$, wherein
  $R^{12}$ and $R^{13}$ represent, independently of each other, a hydrogen atom or an alkyl, aryl, arylalkyl, cycloalkyl, cycloheteroalkyl, heteroalkyl, heteroaryl or heteroarylalkyl group; or
  ($R^{12}$ and $R^{13}$) form together, with the carbon bearing same, a saturated hydrocarbon cycle with 5 or 6 links;
  and $R^{14}$ represents an alkyl, aryl, arylalkyl, cycloalkyl, cycloheteroalkyl, heteroalkyl, heteroaryl or heteroarylalkyl group;

$R_5$ represents a hydrogen atom and $R_4$ represents:
  a phenyl or a benzyl optionally substituted on the phenyl nucleus by:
    1 to 5 halogen atoms such as fluorine or bromine;
    a group $OR^{15}$ or $SR^{15}$, wherein $R^{15}$ represents a hydrogen atom, a benzyl group or a linear or branched saturated or unsaturated hydrocarbon chain, comprising 1 to 4 carbon atoms;
    an amino group;
    a $CF_3$ group;
    a phenyl group; or
    a heteroaromatic cycle with 5 or 6 links;
  a heteroaromatic cycle with 5 or 6 links, comprising 1 or 2 heteroatoms selected from oxygen, nitrogen and sulphur, a nitrogen atom optionally being oxidised in N-oxide form; or
  a methylene group substituted by a saturated or aromatic heterocycle with 5 or 6 links, comprising one or a plurality of heteroatoms selected from sulphur and nitrogen, optionally oxidised in N-oxide or S-oxide form;
or
$R_4$ and $R_5$ form together, with the carbon bearing same:
  a saturated hydrocarbon cycle with 5 or 6 links, or
  a piperidine cycle, nitrogen being situated in position 4 and being optionally substituted by:
    a —$SO_2$-Ph group;
    a $CF_3$ group;
    a $C_1$ to $C_4$ alkyl group;
    a $C_1$ to $C_4$ acyl group;
    a phenyl or a benzyl optionally substituted by one or a plurality of halogen atoms, a $C_1$ to $C_4$ alkyl group or a $C_1$ to $C_4$ alcoxy group; or
    an aromatic heterocycle such as a pyridine or a pyrimidine, optionally substituted by a $C_1$ to $C_4$ alkyl group or a $C_1$ to $C_4$ alcoxy group;

$R_6$ represents:
  a linear or branched saturated or unsaturated hydrocarbon chain, comprising 1 to 6 carbon atoms, and optionally substituted by:
    a group $OR^{16}$, $SR^{16}$, $SOR^{16}$, wherein $R^{16}$ represents a hydrogen atom, a benzyl group or a linear or branched saturated or unsaturated hydrocarbon chain, comprising 1 to 4 carbon atoms;

a COO-Bn or COOH group;
a $SO_3H$ group; or
an amino group; —
a phenyl optionally substituted by one or a plurality of halogen atoms such as fluorine or bromine, or a group: $CF_3$;
$OR^{17}$ wherein $R^{17}$ represents a hydrogen atom, a benzyl group or a linear or branched saturated or unsaturated hydrocarbon chain, comprising 1 to 4 carbon atoms; or
benzyl, or
a benzyl optionally substituted on the phenyl nucleus by:
one or a plurality of halogen atoms, such as fluorine or bromine;
a $CF_3$ group;
a group $OR^{17}$, wherein $R^{17}$ represents a hydrogen atom, a benzyl group or a linear or branched saturated or unsaturated hydrocarbon chain, comprising 1 to 4 carbon atoms; or
a phenyl group; and
$R_7$ represents a radical selected in the group consisting of a hydrogen atom, a benzyl, a $C_2$ to $C_4$ alkyl, —$CHR^{18}$—$COOR^{19}$, —$CHR^{18}$—$OC(=O)R^{19}$ and —$CHR^{18}$—$OC(=O)OR^{19}$, wherein $R^{18}$ and $R^{19}$ represent, independently from each other, an alkyl, aryl, arylalkyl, cycloalkyl, cycloheteroalkyl, heteroalkyl, heteroaryl or heteroarylalkyl group.

In the present invention, the term "pharmaceutically acceptable" refers to that which can be used in the preparation of a pharmaceutical composition which is generally safe, non-toxic and not undesirable, biologically or otherwise, and which is acceptable for veterinary and for human pharmaceutical use.

The term "pharmaceutically acceptable salts" of a compound in the present invention refers to salts which are pharmaceutically acceptable, as defined herein, and which have the desired pharmacological activity of the parent compound. Within the scope of the present invention, they consist of salts obtained with a mineral or organic base. The salt formed thus consists of:
either replacing an acid proton by a metal ion, for example an alkaline metal ion ($Na^+$, $K^+$ or $Li^+$ for example), an alkaline earth metal (such as $Ca^{2+}$ or $Mg^{2+}$) or an aluminium ion,
or coordinating said acid proton with an organic or inorganic base.

Acceptable organic bases include amines such as ammonia, diethanolamine, ethanolamine, N-methylglucamine, triethanolamine, triethylamine, tromethamine and similar. Acceptable inorganic bases include aluminium hydroxide, calcium hydroxide, lithium hydroxide, potassium hydroxide (potash), sodium carbonate and sodium hydroxide (soda).

Advantageously, the pharmaceutically acceptable salts of the compounds according to the invention will be salts obtained with a pharmaceutically acceptable mineral or organic base, such as lithium hydroxide, soda, potash, ammonia, a tertiary amine having the formula $NR_aR_bR_c$, where $R_a$, $R_b$ and $R_c$ represent, independently of each other, an alkyl group as defined below, such as triethylamine, or a basic amino acid such as lysine or arginine and derivatives thereof.

The term "unsaturated" infers, according to the present invention, that the hydrocarbon chain comprises one or a plurality of unsaturations. The term "unsaturation" refers, according to the present invention, to a double or triple bond.

The term "halogen atom" refers, according to the present invention, to a fluorine, chlorine, bromine or iodine atom. Advantageously, it consists of a fluorine, bromine or chlorine atom. More advantageously, it consists of a fluorine or bromine atom, preferably fluorine.

The term "amino" group refers, according to the present invention, to a group having the formula —NR'R", where R' and R" represent, independently of each other, a hydrogen atom or a saturated or unsaturated, linear, branched or cyclic hydrocarbon group, comprising 1 to 6, preferably 1 to 4, carbon atoms, R' and R" not being able to represent a hydrogen atom simultaneously, where R' and R" form together, with the nitrogen atom bearing same, an optionally saturated heterocycle with 5 or 6 links, and not comprising any heteroatoms other than the nitrogen bearing the two radicals R' and R". In particular, the amino group may be an —NHMe, —NHEt, —NHPr, —NHiPr, —NHBu, —NHiBu, —NHtBu, piperidinyl or pyrrolidinyl group.

The term "aryl" group refers, according to the present invention, to an aromatic compound, preferably comprising 5 to 10 carbon atoms, unless specified otherwise, and comprising one or a plurality of attached cycles, such as a phenyl or naphthyl group. Advantageously, it consists of phenyl.

The term "heteroaryl" group refers, according to the present invention, to any aryl group as defined above wherein one or a plurality of carbon atoms has/have been replaced by a one or a plurality of heteroatoms, advantageously 1 to 4 and, more advantageously 1 to 2, such as for example sulphur, nitrogen or oxygen atoms, a nitrogen atom optionally being oxidised in N-oxide form. Examples of heteroaryl groups are the furyl, thienyl, pyrrolyl, pyridinyl, pyrimidyl, pyrazolyl, imidazolyl, tetrazolyl or indyl groups.

The term "heteroaromatic cycle with 5 or 6 links" refers, according to the present invention, to a heteroaryl group as defined above only comprising a single cycle with 5 or 6 links. It particularly consists of a thienyl, pyrrolyl, pyridinyl, pyrimidyl, pyrozolyl, imidazolyl or tetrazolyl group.

The term "heterocycle" refers, according to the present invention, to a hydrocarbon cycle, advantageously with 5 or 6 links, in which one or a plurality of carbon atoms has/have been replaced by one or a plurality of heteroatoms, advantageously 1 to 4 and, more advantageously 1 to 2, such as for example sulphur, nitrogen or oxygen atoms, the sulphur and nitrogen atoms optionally being oxidised in N-oxide and S-oxide form. Unless specified otherwise, this cycle may be saturated or aromatic.

If the heteroatom(s) is/are selected from nitrogen and sulphur, the heterocycle may be one of the following groups: piperidinyl, pyrrolidinyl, pyrrolyl, thienyl, pyrrazolyl, imidazolyl, pyridinyl, pyridazinyl, pyrimidinyl, piperazinyl, thiadiozolyl, tetrahydrothienyl or thiazolyl.

The term "alkyl" refers, according to the present invention, to a linear or branched saturated hydrocarbon chain, comprising 1 to 6 carbon atoms, unless specified otherwise. It particularly consists of methyl, ethyl, n-propyl, isopropyl, n-butyl, iso-butyl, sec-butyl, tert-butyl, n-pentyl, n-hexyl groups.

The term "heteroalkyl" refers, according to the present invention to a linear or branched saturated hydrocarbon chain, comprising 1 to 5 carbon atoms or 1 or 2 heteroatoms, such as sulphur, nitrogen or oxygen atoms.

The term "$C_1$ to $C_4$ acyl" refers, according to the present invention, to an alkyl group as defined above, comprising 1 to 4 carbon atoms, bound with the molecule via a CO group. It may particularly consist of an acetyl, formyl or propionyl group.

The term "cycloalkyl" refers, according to the present invention, to a saturated hydrocarbon cycle comprising 3 to 7, advantageously 5 to 7, carbon atoms, particularly the cyclohexyl, cyclopentyl or cycloheptyl group.

The term "cycloheteroalkyl" refers, according to the present invention, to a cycloalkyl group as defined above wherein one or a plurality of carbon atoms has/have been replaced by one or a plurality of heteroatoms, advantageously 1 to 4 and, more advantageously 1 to 2, such as for example sulphur, nitrogen or oxygen atoms, the sulphur and nitrogen atoms optionally being oxidised in N-oxide and S-oxide form. It may particularly consist of a piperidinyl, pyrrolidinyl, tetrahydrofuryl, tetrahydrothenyl, morpholinyl or piperazinyl group.

The term "alcoxy" refers, according to the present invention, to an alkyl group as defined above bound to the molecule via an oxygen atom. It particularly consists of a methoxy, ethoxy, n-propoxy, isopropoxy, n-butoxy, iso-butoxy, sec-butoxy or tert-butoxy group.

The term "arylalkyl" refers, according to the present invention, to an aryl group as defined above bound to the molecule via an alkyl group as defined above. It particularly consists of a benzyl (Bn) group.

The term "heteroarylalkyl" refers, according to the present invention, to a heteroaryl group as defined bound to the molecule via an alkyl group as defined above. It particularly consists of a thenylmethyl or furylmethyl group.

Advantageously, the radical $R_1$ represents a —C(=O)—O—C($R^8$)($R^9$)—OC(=O)—$R^{10}$ group, wherein:
$R^8$ and $R^9$ represent, independently of each other, a hydrogen atom or an alkyl group; and
$R^{10}$ represents an alkyl group.

In particular, the radical $R_1$ represents the group —(C=O)O—CHMe—OC(=O)CHMe$_2$.

Also advantageously, the radical $R_2$ represents:
an aryl group, optionally substituted by one or a plurality of halogen atoms; or
a linear or branched saturated or unsaturated, preferably saturated, hydrocarbon chain, comprising 1 to 6 carbon atoms, and optionally substituted by a group $OR^{11}$, $SR^{11}$ or $SOR^{11}$ ($R^{11}$ being as defined above) or a phenyl optionally substituted by one or a plurality of halogen atoms such as a fluorine atom.

Preferably, the radical $R_2$ represents an alkyl, aryl or arylalkyl or heteroarylalkyl group, particularly a methyl, phenyl or —CH$_2$CH$_2$Ph group.

According to a first embodiment, which is also the preferred embodiment, the radical $R_3$ represents a hydrogen atom.

Indeed, the inventors surprisingly observed that the compounds according to the invention have a satisfactory activity even when the phosphinic function remains free, contrary to the teaching of the prior art (Hecker S. J. and Erion M. D. J. Med. Chem. 2008, 51, 2328-2345) specifying that activity declines when the phosphinic function is not protected.

According to a second embodiment, the radical $R_3$ represents a group having the formula —C($R^{12}$)($R^{13}$)—OC(=O)—$R^{14}$, where $R^{12}$=$R^{13}$ and $R^{14}$ are as defined above. In particular, the radicals $R^{12}$ and $R^{13}$ represent independently of each other a hydrogen atom or an alkyl group and $R^{14}$ represents an alkyl group. It may be advantageous that $R^{12}$=$R^8$, $R^{13}$=$R^9$ and $R^{14}$=$R^{10}$.

The radical $R_3$ thus advantageously represents a hydrogen atom or a —CHMe—OC(=O)CHMe$_2$ group, and preferably represents a hydrogen atom.

According to one advantageous alternative embodiment of the invention, $R_5$ represents a hydrogen atom and $R_4$ represents a benzyl group optionally substituted by 1 to 5 halogen atoms such as fluorine or bromine, a phenyl or a heteroaromatic cycle with 5 or 6 links. In particular, $R_5$ represents a hydrogen atom and $R_4$ represents a substituted benzyl group, in the para position, by a halogen atom, such as a bromine atom, or by a phenyl.

According to one advantageous alternative embodiment of the invention, $R_4$ and $R_5$ form together, with the carbon bearing same, a cyclohexane or a piperidine cycle, the nitrogen being situated in position 4 and being optionally substituted as defined above for these radicals (in particular, the substituents may be an —SO$_2$-Ph group, a $C_1$ to $C_4$ acyl group, a phenyl group).

Preferably, the radical $R_6$ represents a linear or branched saturated or unsaturated, preferably saturated, hydrocarbon chain, comprising 1 to 6 carbon atoms, and optionally substituted by an SO$_3$H or COOR$^{16}$ group. Advantageously, it consists of an alkyl group such as a methyl group.

Also advantageously, the radical $R_7$ represents a hydrogen atom or an alkyl group, such as an ethyl, or a benzyl or a —CH(CH$_3$)—O—C(=O)—O-Et group. Preferably, this consists of a hydrogen atom or a benzyl group.

According to one advantageous alternative embodiment of the invention, the radicals have the following meaning:
$R_1$ represents a group —C(=O)—O—C($R^8$)($R^9$)—OC(=O)—$R^{10}$, wherein $R^8$ represents a hydrogen atom and $R^9$ and $R^{10}$ represents an alkyl group;
$R_2$ represents an alkyl, phenyl or —CH$_2$CH$_2$Ph group;
$R_3$ represents a hydrogen atom;
$R_5$ represents a hydrogen atom and $R_4$ represents a benzyl group substituted in the para position by a halogen atom (bromine) or by a phenyl; or $R_4$ and $R_5$ form together, with the carbon bearing same, a cyclohexane or a piperidine cycle, the nitrogen being situated in position 4 and being optionally substituted by an —SO$_2$-Ph group, a $C_1$ to $C_4$ acyl group or a phenyl group;
$R_6$ represents an alkyl group;
$R_7$ represents a hydrogen atom or an alkyl group (such as an ethyl) or a benzyl or a —CH(CH$_3$)—O—C(=O)—O-Et group.

According to one particular embodiment, the compound according to the embodiment is selected from the following compounds:

2-(2-Biphenyl-4-ylmethyl-3-{hydroxy-[1-(1-isobutyryloxy-ethoxycarbonylamino)-ethyl]-phosphinoyl}-propionylamino)-propionic acid benzyl ester 2-(2-Biphenyl-4-ylmethyl-3-{hydroxy-[1-(1-isobutyryloxy-ethoxycarbonylamino)-ethyl]-phosphinoyl}-propionylamino)-propionic acid 2-(2-Biphenyl-4-ylmethyl-3-{hydroxy-[1-(1-isobutyryloxy-ethoxycarbonylamino)-ethyl]-phosphinoyl}-propionylamino)-propionic acid ethyl ester 2-(2-Biphenyl-4-ylmethyl-3-{hydroxy-[1-(1-isobutyryloxy-ethoxycarbonylamino)-ethyl]-phosphinoyl}-propionylamino)-propionic ethoxycarbonyloxy acid ester 2-(2-Biphenyl-4-ylmethyl-3-{(1-isobutyryloxy-ethoxy-[1-(1-isobutyryloxy-ethoxycarbonylamino)-ethyl]-phosphinoyl}-propionylamino)-propionic acid 2-(2-(4-Bromo-benzyl)-3-{hydroxy-[1-(1-isobutyryloxy-ethoxycarbonylamino)-ethyl]-phosphinoyl}-propionylamino)-propionic acid benzyl ester 2-(2-(4-Bromo-benzyl)-3-{hydroxy-[1-(1-isobutyryloxy-ethoxycarbonylamino)-ethyl]-phosphinoyl}-propionylamino)-propionic acid 2-[2-Hydroxy-[(1-isobutyryloxy-ethoxycarbonylamino)-phenyl-methyl]-phosphinoylmethyl}-3-(4-thiophen-3-yl-phenyl)-propionylamino]-propionic acid 2-[2-Hydroxy-[(1-isobutyryloxy-ethoxycarbonylamino)-phenyl-methyl]-phosphinoylmethyl}-3-(4-thiophen-3-yl-phenyl)-propionylamino]-3-hydroxypropionic acid 2-(3-Biphenyl-4-yl-2-{hydroxy-[(1-isobutyryloxy-ethoxy-carbonylamino)-thiophen-3-yl-methyl]-phosphinoylmethyl}-propionylamino)-propionic acid 2-{3-Biphenyl-4-yl-2-[hydroxy-[(1-isobutyryloxy-methoxy carbonylamino-ethyl)-phosphinoylmethyl]-propionylamino}-propionic acid 1-(1-{[3-biphenyl-4-yl-2-(1-carboxy-ethylcarbamoyl)-propyl]-hydroxy-phosphinoyl}-ethylcarbamoyloxy)-ethyl acid of 2-dimethyl-propionic acid 2-[(1-{Hydroxy-[1-(1-isobutyryloxy-ethoxycarbonylamino)-ethyl]-phosphinoylmethyl}-cyclopentanecarbonyl)-amino]-propionic acid 2-[(1-Acetyl-4-{hydroxy-[1-(1-isobutyryloxy-ethoxy carbonylamino)-ethyl]-phosphinoylmethyl}-piperidine-4-carbonoyl)-amino]-propionic acid 2-[(4-{Hydroxy-[1-(1-isobutyryloxy-ethoxycarbonylamino)-ethyl]-phosphinoylmethyl}-1-phenyl-piperidine-4-carbonyl)-amino]-propionic acid 2-[(1-Benzenesulfonyl-4-{hydroxy-[1-(1-isobutyryloxy-ethoxycarbonylamino)-ethyl]-phosphinoylmethyl}-piperidine-4-carbonyl)-amino]-propionic acid.

The compounds having formula (I) according to the invention potentially have 3 centres of asymmetry, i.e. the carbons bearing the respective radicals $R_2$, $R_5$ and $R_6$ interacting with the active site of both enzymes. Advantageously, these 3 asymmetric centres are resolved and have a respective absolute configuration optimising the properties of the compounds according to the invention, i.e.:

- the carbon atom bearing the radical $R_2$ has an R configuration (enantiomeric excess greater than 90%);
- if applicable, the carbon atom bearing the radical $R_5$ has an S configuration (ee>90%);
- the carbon atom bearing the radical $R_6$ has an S configuration (ee>90%).

If applicable, the phosphinic acid configuration is left free (it is possible to have one enantiomer, the other enantiomer or a racemic mixture).

Hereinafter, we describe the synthesis of the compounds according to the invention for which the configuration of the 3 asymmetric carbon atoms is resolved and have a respective absolute configuration optimising the properties of the molecules (ee>90%). If desired, those skilled in the art know how to adapt the method described to obtain any desired configuration.

The compounds having formula (Ia) for which $R_5$=H, $R_3$=H and $R_7 \neq$H are obtained by condensing the compounds VI with α-aminoesters VII according to the following schema:

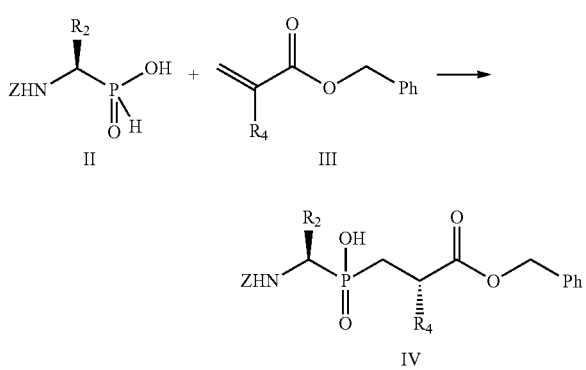

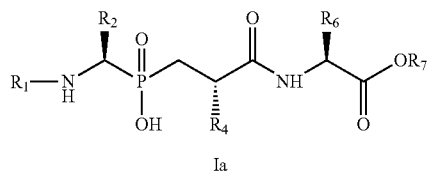

This reaction is performed via the action of a coupling agent such as 1-(3-dimethylaminopropyl)-3-ethylcarbodiimide (EDC) or 2-(1H-benzotriazole-1-yl)-1,1,3,3-tetramethyluronium tetrafluoroborate (TBTU), in the presence particularly of a tertiary amine such as diisopropylethylamine (DIEA). Dimethylformamide (DMF) is advantageously used as a solvent in this step.

The compounds for which $R_5$=H, $R_3$=H and $R_7$=H may be prepared by hydrogenolysis of a compound having formula (Ia) for which $R_7$=Bn, using techniques known to those skilled in the art, particularly in the presence of a catalyst such as palladium on charcoal in a hydrogen atmosphere.

The aminophosphinic compounds (VI) are obtained from compounds (II) and (III):

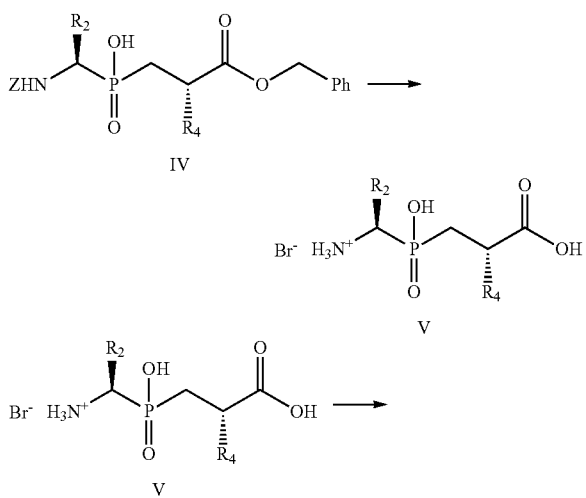

Z represents a benzyloxycarbonyl group.

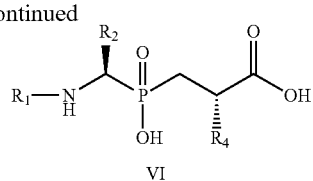

VI

The first step consists of condensing the compounds (II) and (III) in the presence of bis-trimethylsilyl acetamide to produce compound (IV). The reaction is produced advantageously at a temperature between 70 and 120° C., without solvent.

The compound (IV) is obtained in the form of a mixture of diastereoisomers (2R, 4S)/(2R, 4R) in proportions of approximately 65:35. The major stereoisomer (2R, 4S) is then separated from the stereoisomer (2R, 4R) by precipitation in an organic solvent such as ethyl acetate, diethyl ether, isopropanol, acetonitrile or a mixture thereof, and preferably in ethyl acetate, optionally followed by additional purification by means of recrystallisation.

The compound (IV) obtained is thus successively deprotected in the C-terminal position by saponification (NaCH) and in the N-terminal position by means of the action of $HBr/CH_3CO_2H$ to produce a compound (V). The compound (V) is then condensed with an acyloxyalkyl(p-$NO_2$-phenyl) carbonate, prepared as per Alexander et al., 1988, J. Med. Chem., 31, 318, or with an acyloxyalkylsuccinyl carbonate, prepared as per Sun et al. Bioorg. Med. Chem. Lett. 2001, 11, 1875, in dioxane in the presence of $NaHCO_3$.

Alternatively, the compounds (Ia) may be synthesised by condensing (VII) on the intermediate (XI) (Z—NH—CH($R_2$) P(O)OH—$CH_2$CH($R_4$)COOH) obtained by alkaline hydrolysis of the benzyl ester of (IV), under the coupling conditions described above (EDCI or TBTU in the presence of DIEA in DMF). The compound (XII) is thus obtained, which after deprotecting the Z group, gives rise to the compound (XIII). This gives rise to (Ia) using the methods described above for the conversion of (V) to (VI).

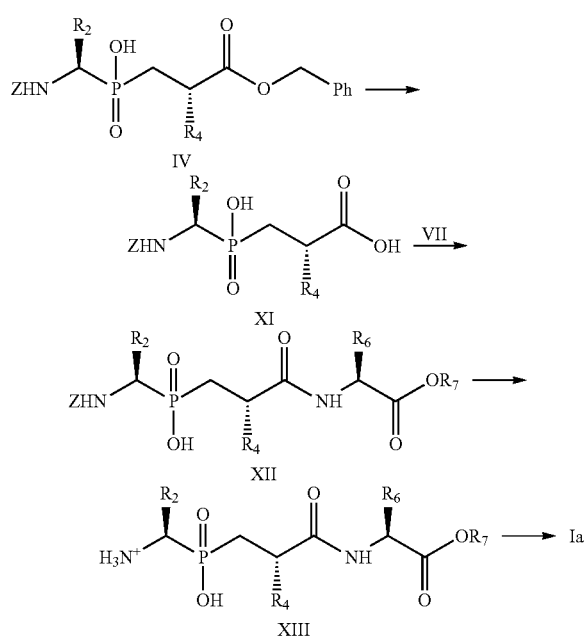

The optically pure compounds (II), having an (R) configuration are prepared from the aldehydes (VIII) according to the synthesis protocol and the resolution method described by Baylis et al. in J. Chem. Soc. Perkin Trans I (1984), 2845.

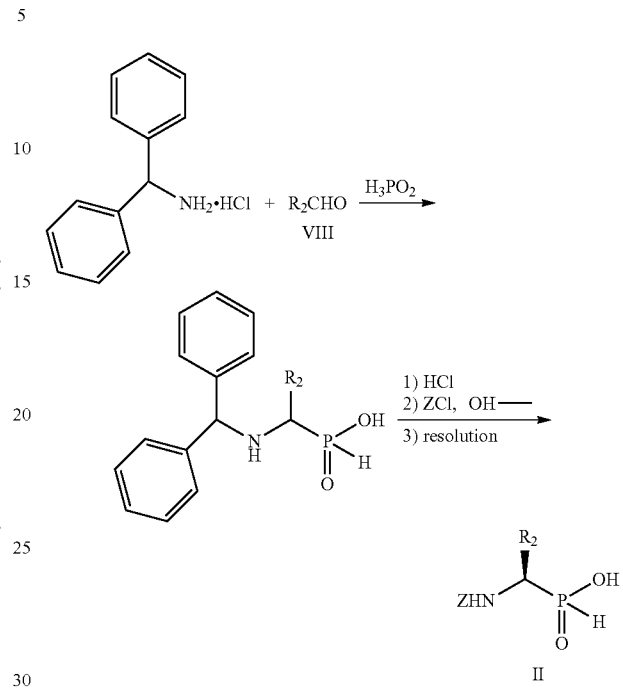

Z represents a benzyloxycarbonyl group.

The benzyl ester of the acrylates (III) is prepared from the corresponding acrylic acids (X) via the action of benzyl bromide in the presence of $K_2CO_3$ in acetonitrile at 80°. The acids (X) are obtained by means of a conventional protocol, well known to those skilled in the art, comprising the following steps: condensation of an aldehyde (IX) on diethylmalonate (step 1), reduction of the double bond and saponification of the ester functions (step 2: 1)$NaBH_4$, 2)$OH^-$, 3)$H^+$) and Mannich reaction (step 3).

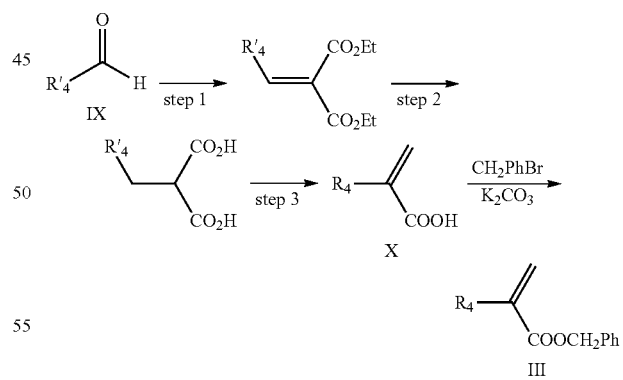

The compounds having formula (Ib), for which $R_5 \neq H$ and $R_3 = H$, are obtained by means of the same coupling as that described for the compounds (Ia) by replacing the intermediate (VI) by the analogue (VIbis) thereof.

This is obtained by condensing protected aminophosphinic acid (IIbis) and an activated alcohol in the form of mesylate or triflate (XIV) in the presence of lithium diisopropyl amide (LDA) (McKittrick et al. in Bioorg. Med. Chem. Lett. (1996), 1629).

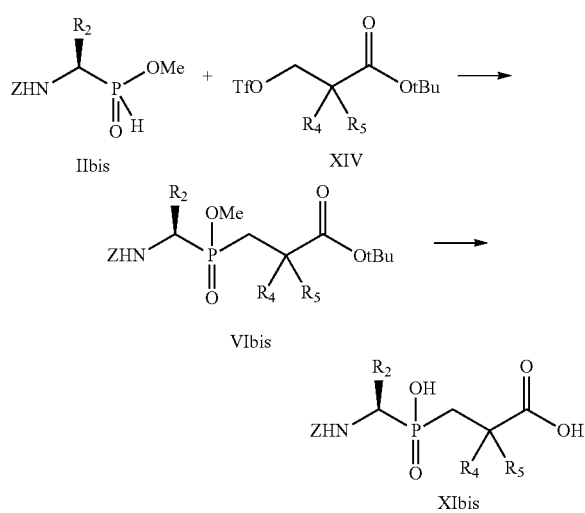

IIbis    XIV

VIbis

XIbis

Z represents a benzyloxycarbonyl group.

The compounds (XIV) are prepared from the corresponding carboxylic acid having the formula $CH(R_4)(R_5)$—$CO_2H$. After esterification in t-butyl ester form to produce $CH(R_4)(R_5)$—$CO_2tBu$ (XV), treatment with paraformaldehyde in the presence of Lithium diisopropylamide ($iPr_2NLi$) produces the alcohol ester $HOCH_2$—$C(R_4)(R_5)$—$COOtBu$. The alcohol function is then activated in the form of mesylate or triflate to produce the compound (XIV).

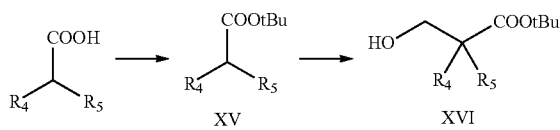

XV    XVI

The carboxylic acid tButyl and phosphinic acid methyl esters of the compound (VIbis) are deprotected with TFA in methylene chloride to produce the compound (XIbis). The end of the synthesis is conducted as described above.

The compounds having formula (Ic) for which $R_3\#H$ and $R_7\#H$ are prepared from the corresponding compounds (Ia) and (Ib) for which $R_3$=H. The alkylation of the phosphinic function is obtained by means of the action of a halageno (acyloxy)alkyl (the halogen is a chlorine or a bromine). This alkylation is performed in the presence of tetrabutylammonium sulphate, DIEA, NaI in a solvent such as toluene or chloroform, preferably toluene. The optional deprotection of the carboxylate function ($R_7$=H) is obtained as above by hydrogenolysis of the benzyl ester ($R_7$=$CH_2Ph$).

More generally, the present invention relates to a method for preparing a compound having formula (I) as defined above, according to the following steps:
peptide coupling between a compound having the following formula (A):

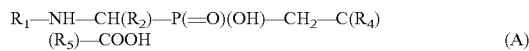

and a compound having the following formula (B):

to produce a compound (I) wherein $R_3$=H and $R_1, R_2, R_4, R_5, R_6$ and $R_7$ are as defined above, $R_7$ however not representing a hydrogen atom;

optionally a substitution step of the phosphinic acid function by an $R_3\#H$ group,
optionally a hydrolysis step (saponification or hydrogenolysis) of the —$COOR_7$ function;
separation of the reaction medium of the compound (I) obtained in any of the above steps.

The method may be followed by optional additional substitution and/or protection/deprotection reaction well known to those skilled in the art. The reaction medium separation step may be performed using methods well known to those skilled in the art, such as by extraction, evaporation of the solvent or by precipitation and filtration. The compound obtained may then be purified if required using techniques well known to those skilled in the art, such as by recrystallisation if the compound is crystalline, by distillation, by silica gel column chromatography or by high performance liquid chromatography (HPLC).

The present invention also relates to a compound having formula (I) as defined above for the use thereof as a medicinal product, particularly for the treatment of pain and in particular (1) neuropathic or neuroinflammatory pain or (2) sharp pain (particularly acute pain).

The term "neuropathic or neuroinflammatory pain" refers more specifically, but non-exhaustively, to the pain caused by diabetes mellitus type I or II, viral or retroviral infection, cancer chemotherapy, radiotherapy, a surgical procedure including amputee illusion and the after-effects of mastectomy, alcoholism, facial neuralgia, trauma such as brachial plexus syndrome, radiculopathy or radiculagia such as sciatica, cruralgia or thoracic outlet syndrome, fibromyalgia, restless leg syndrome, inflammatory joint pain caused particularly by arthritis or an acute phase of arthrosis, degenerative joint pain caused particularly by arthrosis, or lumbago.

This neuropathic and neuroinflammatory pain is characterised by: i) excessive nociception referred to as "hyperalgia", assessed using suitable tests on predictive animal models such as the Plantar test or the hot plate; ii) allodynia consisting of a painful sensation from a region not concerned by the original nociceptive stimulus and the reduction of which is particularly measured using the Von Frey test.

Sharp pain is caused by the stimulation of receptors, channels or other targets transmitting a message interpreted as being an acute pain to the brain. The term "sharp pain" refers particularly to postoperative pain, pain in subjects suffering from cancer, pain caused by peripheral tissue lesions inducing an excessive painful influx in the nervous system. This applies particularly to burns, trauma, postoperative effects and a large number of diseases, giving rise either to acute pain (postoperative, trauma-induced, infectious, degenerative conditions) or chronic pain (variably progressive persistent lesional conditions).

The invention also relates to the use of a compound according to the invention for the production of a medicinal product for the treatment of pain and particularly (1) neuropathic or neuroinflammatory pain or (2) sharp pain. The invention also relates to a method for treating pain and particularly (1) neuropathic or neuroinflammatory pain or (2) sharp pain, comprising the administration of an effective quantity of at least one compound according to the invention to a patient requiring same.

The present invention also relates to a pharmaceutical composition comprising at least one compound having formula (I) as defined above and at least one pharmaceutically acceptable vehicle. The compounds according to the invention may be administered by the oral, sublingual, parenteral, subcutaneous, pulmonary, nasal, intramuscular, intravenous, intrathecal, intra-articular or transdermal route. The active ingredient may be administered in unit dose forms, mixed with conventional pharmaceutical media, to animals or humans. This composition may comprise, in the same formulation or in association in a different form, at least one further active substance, particularly an analgesic selected in the group consisting of morphine and the derivatives thereof, tetrahydrocannabinol and the derivatives thereof, Gaba derivatives (Gabapentin or Pregabalin), botulinum toxins (botulinum toxin A) or a purinergic receptor antagonist (P2X3 receptor).

The present invention also relates to a pharmaceutical composition comprising:

(i) at least one compound having formula (I) as defined above, and (ii) at least one further active substance, selected in the group consisting of morphine and the derivatives thereof, tetrahydrocannabinol and the derivatives thereof, Gaba derivatives (Gabapentin or Pregabalin), botulinum toxins (botulinum toxin A) and a purinergic receptor antagonist (P2X3 receptor), as combination products for simultaneous, separate or staggered use.

These compositions and the compounds having formula (I) may be used as medicinal products.

According to one advantageous alternative embodiment of the invention, the compounds are intended for the treatment of neuropathic or neuroinflammatory pain and are administered orally.

The pharmaceutical composition will thus be preferably formulated for oral administrations. The suitable unit dose forms include tablets, capsules, powders, granules and solutions for oral suspensions; the main active ingredient is mixed with a suitable pharmaceutical vehicle. The formulation may be such that it has a sustained or delayed activity and that it releases a predetermined quantity of active substance continuously.

The inventors observed that the compounds, administered orally, do not pass the blood-brain barrier (BBB) and thus do not enter the brain. Under these conditions, any undesirable side effects, even slight, of cerebral endogenous opioids (enkephalins) (F. Noble and B. P. Rogues, Exp. Op. Ther. Targets, 2007, 11, 145-159) liable to arise from the activation of opioid brain receptors, by these enkephalins protected by inactivation by the compounds according to the invention, are completely ruled out.

This composition may comprise at least one further active substance. In particular, this pharmaceutical composition may comprise an analgesic selected from the group consisting of Gaba derivatives such as Gabapentin or Pregabalin, or a P2X3 purinergic receptor antagonist and botulinum toxins such botulinum toxin A. For example the compounds having formula (I) formulated for oral administration may be used in association with locally injected botulinum toxin.

According to a second advantageous alternative embodiment of the invention, the compounds are intended for the treatment of nociceptive pain and are administered by a route other than the oral route, such as for example by the sublingual, parenteral, subcutaneous, pulmonary, nasal, intramuscular, intravenous, intrathecal, intra-articular or transdermal route, particularly the intravenous route.

The active ingredient may be administered in unit dose forms, mixed with conventional pharmaceutical media, to animals or to humans. The pharmaceutical composition will thus be formulated for intravenous administration.

A further analgesic such as morphine or the derivatives thereof, tetrahydrocannabinol or the derivatives thereof, or a P2X3 purinergic receptor antagonist may be used in association (as combination products for simultaneous, separated or staggered use).

According to any of the alternative embodiments envisaged, the compounds according to the invention may be used at doses between 0.01 mg and 1000 mg per day, administered in a single dose once daily or administered in a plurality of doses throughout the day, for example twice daily in equal doses. The daily dose administered is advantageously between 0.01 mg and 100 mg or more advantageously between 0.1 mg and 10 mg.

FIGURES

Key of Figures

In all the figures, the statistical analyses (p, Student's test) are indicated as follows:

★$p<0.1$ versus control
★★$p<0.01$ versus control
★★★$p<0.001$ versus control

FIG. 1 represents the total paw licking time (expressed in seconds during the 5 min examination period) by a mouse receiving formalin as a function of time (minutes) after oral administration of the vehicle (□) or a compound according to the invention (■), graphs (A), (B) and (C) corresponding to the compounds from examples 8, 3 and 4, respectively.

Figure 2:
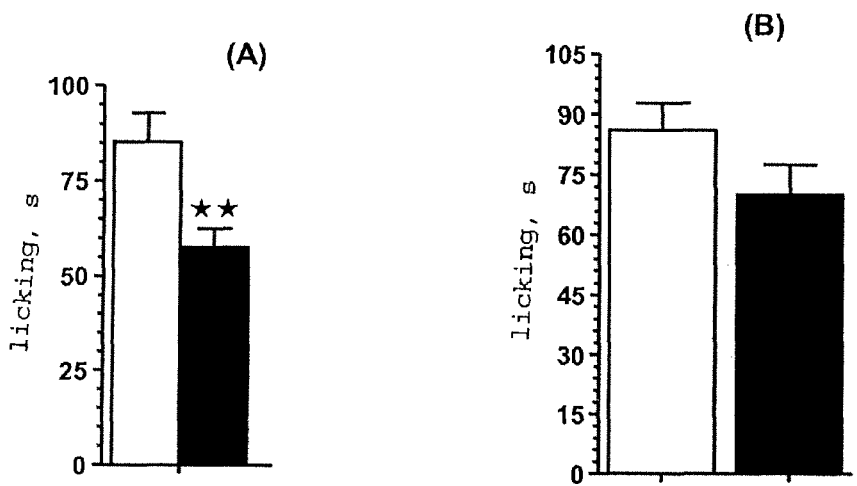

FIG. 2 represents the total paw licking time (expressed in seconds during the 5 min examination period) by a mouse receiving formalin as a function of time (minutes), 90 min after oral administration: (A) of the vehicle (□) or of compound 8 (50 mg/kg) according to the invention (■) or (B) of the vehicle (□) or of the reference molecule (100 mg/kg) (■).

Figure 3:
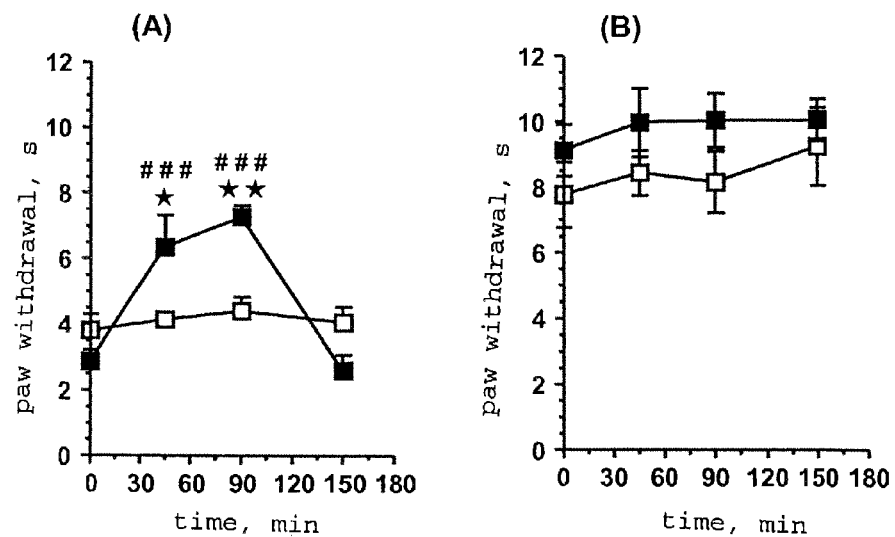

FIG. 3 represents the response obtained in a neuropathic pain model induced by partial and unilateral ligation of the sciatic nerve of a mouse (Plantar test), for evaluating thermal hyperalgia. After oral administration of the vehicle (□) or the compound from examples 3 (50 mg/kg) (■), paw withdrawal is measured (in seconds) as a function of time (in minutes) 14 days after surgery. Graph (A) represents the response observed for the ipsilateral paw, whereas graph (B) represents the response obtained for the contralateral paw.

(mean of contralateral paws at 90 min: vehicle (7.85), compound 3=9.4 s)

Figure 4:
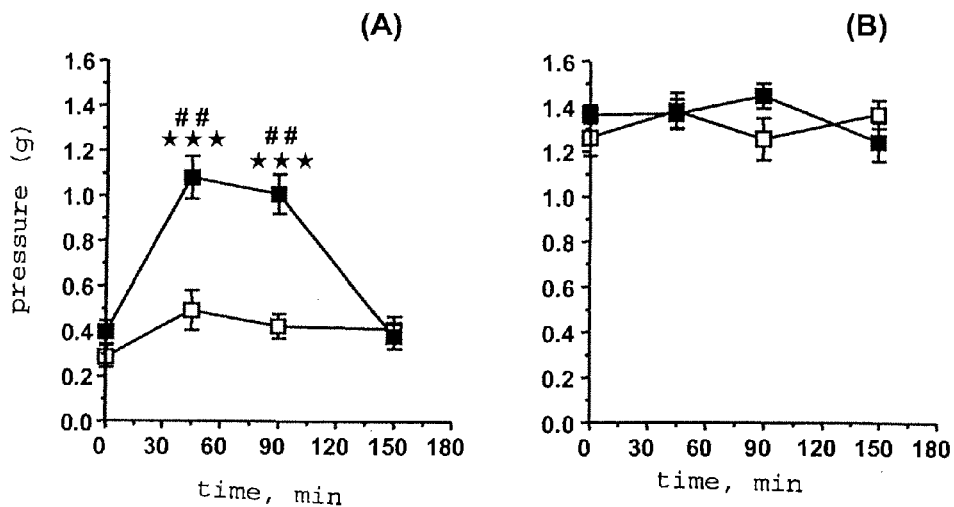

FIG. 4 represents the response obtained in a Von Frey test (allodynia measurement) at a pressure (in g) of a mouse paw using filaments of increasing hardness, as a function of time (min) 14 days after surgery and after oral administration of the vehicle (□) or the compound from example 3 (50 mg/kg) (■). Graph (A) represents the response observed for the ipsilateral paw, whereas graph (B) represents the response obtained for the contralateral paw.

Figure 5:
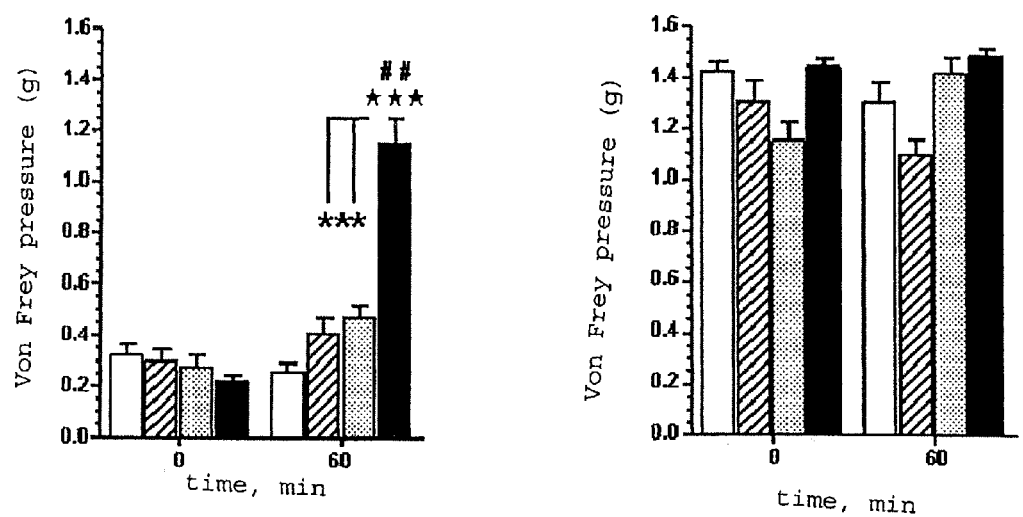

FIG. 5 represents the responses obtained at 60 min in a Von Frey test, as described in the key in FIG. 4. The compound from example 4 is administered alone orally at a dose of 10 mg/kg (▨) and gabapentin, also orally at a dose of 30 mg/kg (▨) These two compounds are administered orally, in association, at the above doses (■). The control (□) corresponds to the oral administration of the vehicle.

EXAMPLES

The following examples are used to illustrate the invention without limiting same. The following abbreviations have been used:

TLC Thin Layer Chromatography
HPLC High Performance Liquid Chromatography
DMSO Dimethylsulphoxide
eq. Equivalent
ESI Electrospray ionisation min Minutes
NMR Nuclear Magnetic Resonance
TFA Trifluoroacetic acid

Example 1

(R)(1-Benzyloxycarbonylamino-ethyl)-phosphinic acid

Step 1: (1-((diphenylmethyl)amino-ethyl)phosphinic acid

A mixture of 200 g (0.91 mole) of diphenylamethylamine hydrochloride in 600 ml of water and 132 ml (1.0 mole) of phosphinic acid (50% in water) is boiled under reflux with stirring. 56 ml (1.0 mole) of acetaldehyde in solution in 350 ml of water is added drop by drop in 30 min.

The reaction is followed by HPLC. After 2 hours, the reaction is returned to ambient temperature. The white precipitate obtained is filtered, washed with water (2×300 ml) and acetone (2×300 ml) and dried. White solid, 225 g (90%).

Step 2: (1-aminoethyl)-phosphinic acid

A mixture of 225 g of the compound from step 1 and 2 l of 6N HCl is boiled under reflux for 5 hours. After cooling, the reaction medium is concentrated by half and extracted with 3×1.5 l of ethyl ether. The solution is evaporated to dryness and the oily residue (130 g) is taken up with 1.3 l of ethanol. The solution is cooled to 0° C. and 450 ml of propylene oxide is added. A white solid precipitates. The precipitate is dewatered, washed with ethanol (2×100 ml), ethyl ether (2×100 ml) and dried. White solid, 65 g (73%).

(1H) NMR DMSO d6 δ (ppm): 1.26 (3H d,d); 3.32 (1H m); 6.98 (1H d); 8.23 (3H s).

Step 3: (R)(1-benzyloxycarbonylamino-ethyl-phosphinic acid

In 300 ml of water, 65 g (0.59 mole) of the compound from step 2 is solubilised and the pH is adjusted to 93.5 by adding sodium hydroxide. 85 ml of benzyl chloroformiate is added under stirring. After 1 hour at 0° C., the mixture is returned to ambient temperature and is poured onto a mixture of ice (1 l) and concentrated HCl (300 ml). The white precipitate formed is dewatered, washed with water (2×100 ml) and dried. White solid, 131 g (91%).

HPLC(CH$_3$CN (0.1% TFA)/H$_2$O (0.1% TFA) 30:70, Kromasil C18 column), Rt 4.6 min.

The resolution of the racemic phosphinic acid is performed by recrystallisation of the salt obtained with the (R)(+) α-methylbenzylamine, as described in Baylis et al. (J. Chem. Soc. Perkin Trans 11984, 2845) in an ethyl acetate/isopropanol mixture=3.5:1. White solid, 48 g (86%).

(1H) NMR DMSO d6 δ (ppm): 1.19 (d, 3H); 3.66 (m, 1H); 5.03 (s, 2H); 6.78 (d, 1H); 7.35 (s, 5H); 7.62 (d, 1H)

Example 2

2-biphenyl-4-ylmethyl-acrylic acid benzyl ester

Step 1: 2-biphenyl-4-ylmethyl-malonic acid

The protocol used is that described in Organic Synthesis Coll. Vol. 3 p. 337. Using 48.4 g of diethylmalonate and 50 g of diphenyl-4-carboxaldehyde, 88.2 g of diethyl 2-biphenyl-4-ylmethylene-malonic acid ester is obtained.

This compound (88 g) is placed in solution in ethanol (500 ml) and the double bond is reduced by the action of sodium borohydride (10.3 g). After 1 hour, the reduction is completed and the reaction mixture is diluted in ethanol (500 ml) and 1.36 l of 1N NaOH is added at 0° C.

After evaporating the ethanol and acidifying the aqueous phase, 2-biphenyl-4-ylmethyl-malonic acid is obtained in the form of a white solid, 64.8 g (88%).

HPLC(CH$_3$CN (0.1% TFA)/H$_2$O (0.1% TFA) 30:70, Kromasil C18 column), Rt 3.5 min.

Step 2: 2-biphenyl-4-ylmethyl-acrylic acid

The diacid obtained in step 1 (60 g) is solubilised in 300 ml of THF and 23.5 ml (2 eq.) of diethylamine and 19.5 ml (4 eq.) of formaldehyde are added. The reaction medium is boiled under reflux with stirring for 20 hours. After cooling, the THF is evaporated and the residue is taken up with ethyl acetate (500 ml) and acidified with 100 ml of 6N HCl. The organic phase is retrieved, washed with 2×350 ml of water, 1×300 ml of sat. NaCl and dried over Na$_2$SO$_4$. A white powder is obtained, 51 g (97%).

HPLC (CH$_3$CN (0.1% TFA)/H$_2$O (0.1% TFA) 30:70, Kromasil C18 column), Rt=6.2 min.

Step 3: 2-biphenyl-4-ylmethyl-acrylic acid benzyl ester 2-biphenyl-4-ylmethyl-acrylic acid (30 g) is suspended in 300 ml of acetonitrile. 21 g of K$_2$CO$_3$ followed by 16.5 g of benzyl bromide are added and heated to 80° C. for 15 hours. The reaction medium is evaporated and the residue taken up with ethyl acetate. The organic phase is washed with a Na$_2$CO$_3$ solution, water and with a saturated NaCl solution, and dried on Na$_2$SO$_4$. After filtration, the organic phase is evaporated to dryness. Oily product, 40 g (96%).

HPLC (CH$_3$CN (0.1% TFA)/H$_2$O (0.1% TFA) 80:20, Kromasil C18 column), Rt=12.7 min.

NMR DMSO d6 δ (ppm): 3.6 (2H s); 5.1 (2H s); 5.5 (1H d); 6.2 (1H d); 7.1-7.5 14H m).

Example 3

2-(2-biphenyl-4-ylmethyl-3-{hydroxy-[1-(1-isobutyryloxy-ethoxycarbonylamino)-ethyl]-phosphinoyl}-propionylamino)-propionic acid benzyl ester

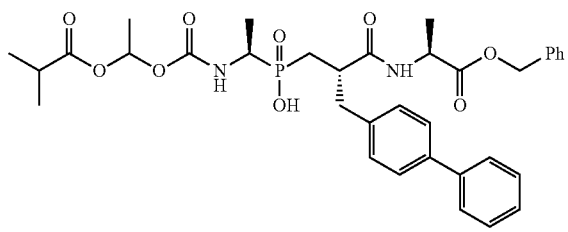 [SMILES: CC(OC(=O)N[C@@H](C)P(=O)(O)C[C@@H](Cc1ccc(-c2ccccc2)cc1)C(=O)N[C@@H](C)C(=O)OCc1ccccc1)OC(=O)C(C)C]

Step 1: 3-[(2-benzyloxycarbonyl-3-biphenyl-4-yl-propyl)-hydroxy-phosphinoyl]-butyric acid benzyl ester The aminophosphinic synthon from example 1 (9.6 g) and the 2-biphenyl-4-ylmethyl-acrylic acid benzyl ester from example 2, step 3 (14.3 g) are added to 21 ml of bis-trimethylsilylacetamide (BSA) and the reaction mixture is stirred for 5 hours at 70° C. After cooling, the mixture is diluted in ethyl acetate. A few drops of water are added until a precipitate is formed. The suspended solid is stirred for 1 hour at ambient temperature and is dewatered, washed with ethyl acetate and vacuum-dried. 11.6 g (79%) of (R)(S) configuration diastereoisomer is obtained.

HPLC (CH$_3$CN (0.1% TFA)/H$_2$O (0.1% TFA) 55:45, Kromasil C18 column), Rt=17.8 min.

1H NMR (DMSO) d6 δ (ppm) 1.26 (3H dd); 1.81-2.16 (2H m); 2.78-3.12 (3H m); 3.78 (1H qt); 4.94-5.08 (2×2H 2q); 7.12-7.68 (19H arom.) +NH (m).

Step 2: 1-[(3-biphenyl-4-yl-2-carboxy-propyl)hydroxy-phosphinoyl]-ethyl ammonium hydrobromide The compound from step 1 (10.6 g) is suspended in THF (100 ml) and 7.4 g of sodium hydroxide in solution in 50 ml of water is added with stirring at 0° C. The mixture is stirred at ambient temperature overnight. The THF is evaporated, the aqueous phase is acidified to pH 1 with 1N HCl, and extracted with ethyl acetate. The organic phase is dried on Na$_2$SO$_4$, filtered and evaporated to dryness. White solid, 7.4 g (83%).

The acid obtained (6 g)) is placed in solution in 60 ml of hydrobromic acid (45% in CH$_3$CO$_2$H) and the solution is stirred for 1 hour at ambient temperature.

The reaction mixture is then evaporated to dryness and vacuum-dried to produce an orangey gummy product, 6.9 g (99%).

Step 3: 2-biphenyl-4-ylmethyl-3-{hydroxy-[1-(1-isobutyryloxy ethoxycarbonylamino)-ethyl]-phospinoyl}-propionic acid The compound from step 2 (6.23 g) is suspended in acetonitrile (70 ml). 9.8 g (8 eq.) of NaHCO$_3$ in solution in 70 ml of water and 4.76 g (1.1 eq.) of isobutyric acid 1-[2-(4-nitrophenyl)-acetoxy]-ethyl ester are successively added. The mixture is stirred at ambient temperature overnight.

After evaporation of the acetonitrile, the aqueous phase is extracted with ethyl acetate. The organic phase is washed with 10% citric acid, a saturated aqueous NaCl solution, dried over Na$_2$SO$_4$, filtered and evaporated to dryness. The unprocessed product is chromatographed on silica gel using the 9:1 CH$_2$Cl$_2$/MeOH mixture followed by 7:3 as an eluent. White solid, 4.42 g (60%).

HPLC (CH$_3$CN (0.1% TFA)/H$_2$O (0.1% TFA) 50:50, Kromasil C18 column), Rt=3.7 min.

NMR (DMSO d6) δ ppm: 0.95-1.45 (12H m); 1.63-2.15 (2H m); 2.45 (1H m); 2.81-3.03 (3H m); 3.68 (1H m); 6.63 (1H m); 7.20-7.82 (10H m).

Step 4: 2-(2-biphenyl-4-ylmethyl-3-{hydroxy-[1-(1-isobutyryloxy-ethoxycarbonylamino)-ethyl]-phosphonoyl}-propionylamino)-propionic acid benzyl ester The compound from step 3 (500 mg) is placed in solution in dimethylformamide (DMF) (10 ml) and 945 mg (3 eq.) of TBTU, 1 ml of DIEA (6 eq.) and 257 mg (1.2 eq.) of the alanine benzyl ester hydrochloride are successively added. The mixture is stirred at ambient temperature for 15 min and the DMF is evaporated. The residue is taken up with ethyl acetate, and successively washed with a 10% citric acid solution, water, a 10% NaHCO$_3$ solution, a saturated aqueous NaCl solution and is dried over Na$_2$SO$_4$. After filtering, the solution is evaporated in a vacuum. White solid, 1 g (95%).

HPLC (CH$_3$CN (0.1% TFA)/H$_2$O (0.1% TFA) 50:50, Kromasil C18 column), Rt=8.2 min.

1H NMR (DMSOd6) δ (ppm): 0.98-1.42 (15H m); 1.48-1.82 (2H m); 2.45 (1H m); 2.69-3.05 (3H m); 4.33 (1H m); 5.06 (2H s); 6.62 (1H m); 7.21-7.67 (15H m); 8.45 (1H t).

Example 4

2-(2-biphenyl-4-ylmethyl-3-{hydroxy-[1-(1-isobutyryloxy-ethoxycarbonylamino)-ethyl]-phosphinoyl}-propionylamino)-propionic acid

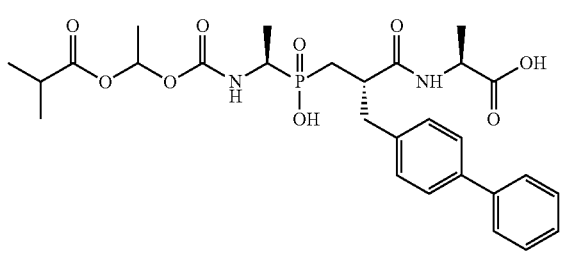 [SMILES: CC(OC(=O)N[C@@H](C)P(=O)(O)C[C@@H](Cc1ccc(-c2ccccc2)cc1)C(=O)N[C@@H](C)C(=O)O)OC(=O)C(C)C]

250 mg of the compound from example 3 is solubilised in 10 ml of MeOH and 125 mg of 10% Pd/C is added. The mixture is hydrogenolysed at standard temperature and pressure in a hydrogen atmosphere.

After 1 hour, 20 ml of CH$_2$Cl$_2$ is added and the whole is filtered on Celite. It is evaporated to dryness and vacuum-dried. White solid 184 mg (89%).

HPLC (CH$_3$CN (0.1% TFA)/H$_2$O (0.1% TFA) 60:40, Kromasil C18 column), Rt=4.1 min.

ESI(+) [M+H]$^+$ mass=577

(1H) NMR DMSO d6, δ (ppm): 1-1.5 (15H m); 1.5-2.0 (2H m); 2.5 (1H, m); 3.0 (3H m); 3.7 (1H m); 4.2 (1H m); 6.2 (1H m); 7.3-7.7 (9H+1H m); 8.4 (1H dd).

Example 5

2-(2-biphenyl-4-ylmethyl-3{hydroxy-[1-(1-isobutyryloxy-ethoxycarbonylamino)-ethyl]-phosphinoyl}-propionylamino)-propionic acid sodium salt 87 mg of the compound from example 4 is dissolved in a mixture of 1 ml of water and 1 ml of acetonitrile. 12.6 mg of NaHCO$_3$ is added. The solution obtained is freeze-dried and produces 87 mg of the expected compound.

Example 6

2-(2-biphenyl-4-ylmethyl-3-{hydroxy-[1-(1-isobutyryloxy-ethoxycarbonylamino)-ethyl]-phosphinoyl}-propionylamino)-propionic acid ethyl ester

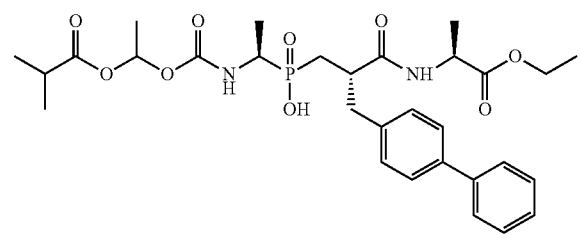 [SMILES: CCOC(=O)[C@H](C)NC(=O)[C@H](Cc1ccc(-c2ccccc2)cc1)CP(=O)(O)[C@H](C)NC(=O)OC(C)OC(=O)C(C)C]

The compound from example 3 (500 mg) is coupled under the conditions in step 4 of example 3 with alanine ethyl ester hydrochloride (152 mg). The crude product obtained is chromatographed on silica gel using the 7:3:0.2 CH$_2$Cl$_2$/MeOH/AcOH mixture. White solid, 530 mg (88%).

ESI(+) [M+H]$^+$ mass=605

1H NMR (DMSO d6) δ (ppm): 1.0-1.5 (18H m); 1.6-1.9 (2H m); 2.5 (1H m); 2.7-3.0 (3H m); 3.7 (1H m); 4.0 (2H q); 4.2 (1H qt); 6.6 (1H m); 7.2-7.7 (9H+1H m); 8.4 (1H dd).

Example 7

Alanine 1-ethoxycarbonyloxyethyl ester trifluoroacetate

Step 1: N-terbutyloxycaronyl-L-alanine 1-ethoxycarbonyloxyethyl ester

N-boc-L-alanine (boc=tert-butyloxycarbonyl) (10 g) is placed in solution in 100 ml of ethyl acetate in the presence of triethylamine (6.4 g, 1.2 eq.) in an inert atmosphere and the mixture is stirred for 15 min at ambient temperature. NaI (1.9 g, 0.2 eq.) is then added and 1-chloroethylethylcarbonate (9.38 g, 1.1 eq.). The mixture is boiled under reflux for 15 hours. When the reaction is complete, the mixture is washed with a 10% aqueous NaHCO$_3$ solution (twice), H$_2$O, and a saturated aqueous NaCl solution. Slightly yellow oil. 12.9 g (80%).

TLC (cyclohexane/EtOAc: 6:4) Rf=0.73.

Step 2: L-alanine 1-ethoxycarbonyloxyethyl ester trifluoroacetate

The compound from step 1 (12.9 g) is solubilised in 25 ml of CH$_2$Cl$_2$ and 25 ml of trifluoroacetic acid is added at 0° C. The mixture is stirred at ambient temperature for 3 hours. When the reaction is complete, the reaction mixture is evaporated to dryness. The residue is taken up 3 times with cyclohexane and the mixture is re-evaporated to remove the excess TFA. Slightly brown oil, 13.4 g (99%).

1H NMR (DMSO d6) δ (ppm): 1.2 (3H t); 1.35 (3H dd); 1.45 (3H d); 4.1 (2H q); 6.7 (1h m); 8.3 (3H s).

Example 8

2-(2-biphenyl-4-ylmethyl-3-{hydroxy-[1-(1-isobutyryloxy-ethoxycarbonylamino)-ethyl]-phosphinoyl}-propionylamino)-propionic acid 1-ethoxycarbonyloxy-ethyl ester

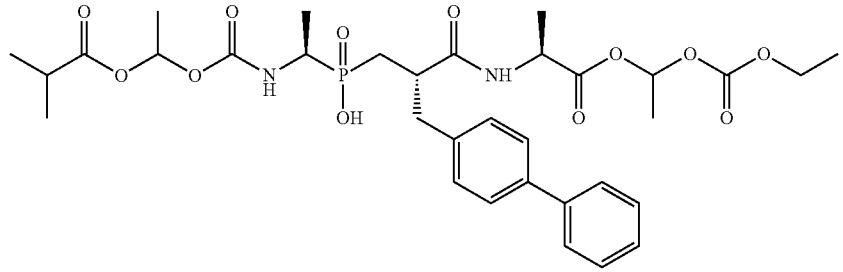 [SMILES: CCOC(=O)OC(C)OC(=O)[C@H](C)NC(=O)[C@H](Cc1ccc(-c2ccccc2)cc1)CP(=O)(O)[C@H](C)NC(=O)OC(C)OC(=O)C(C)C]

The compound from example 3 (500 mg) is coupled, under the conditions of step 4 of example 3, with the compound from example 7, (500 mg, 1.2 eq.)). The crude product is chromatographed on silica gel (CH$_2$Cl$_2$/MeOH/AcOH: 7:3:0.2). White solid, 330 mg (55%).

HPLC (CH$_3$CN (0.1% TFA)/H$_2$O (0.1% TFA) 70:30, Kromasil C18 column), Rt=5.4 min.

ESI(+) [M+H]$^+$ mass=693

1H NMR (DMSOd6) δ (ppm): 1.0-1.4 21Hm); 1.5-2.0 (2H m); 2.5 (1Hm); 2.7-3.0 (3Hm); 3.65 (1Hm), 4.15 (2H q); 4.25 (2H m); 6.6 (2H m); 7.2-7.7 (9H+1H m); 8.5 (1H dd).

Example 9

2-(2-biphenyl-4-ylmethyl-3-{(1-isobutyryloxy-ethoxy)-[1-(1-isobutyryloxy-ethoxycarbonylamino)-ethyl]-phosphinoyl}-propionylamino)-propionic acid

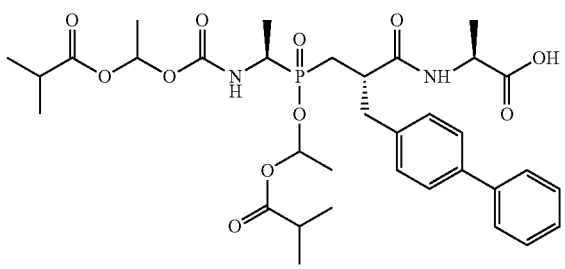 [SMILES: CC(OC(=O)N[C@@H](C)P(=O)(C[C@@H](Cc1ccc(-c2ccccc2)cc1)C(=O)N[C@@H](C)C(=O)O)OC(C)OC(=O)C(C)C)OC(=O)C(C)C]

Step 1: Isobutyric acid 1-{1-[[2-(1-benzyloxycarbonyl-isobutyryloxy-ethoxy)-phosphinoyl]-ethylcarbamoyloxy}-ethyl ester The final compound from example 3 (350 mg) is placed in solution in toluene. In an inert atmosphere, 90 mg of tetrabutylammonium sulphate, (nBu)$_4$N$^+$SO$_4$H$^-$ (0.5 eq.), NaI (80 mg, 1 eq.), isobutyric acid 1-chloroethyl ester (160 mg, 4 eq.) and 0.9 ml of DIEA are added. The mixture is heated to 120° C. for 3 hours. The reaction mixture is returned to ambient temperature and is diluted in 50 ml of ethyl acetate, the solution obtained is washed with water, with a 10% NaHCO$_3$ aqueous solution, with a saturated aqueous NaCl solution and dried over Na$_2$SO$_4$. After filtration, the solvents are evaporated and the residue (400 mg) is purified by means of silica gel chromatography with the 90:10 CH$_2$Cl$_2$/MeOH mixture as the eluent. Yellow oil, 200 mg.

HPLC (CH$_3$CN (0.1% TFA)/H$_2$O (0.1% TFA) 80:20, Kromasil C18 column), Rt=8.8 min.

ESI(+) [M+H]$^+$ mass=781.

Step 2: 2-(2-biphenylk-4-ylmethyl-3-{(isobutyryloxy-ethoxy)-[1-(1-isobutyryloxy-ethoxycarbonylamino)-ethyl]-phosphinoyl}-propionylamino)-propionic acid The compound from step 1 (200 mg) is solubilised in MeOH (10 ml). 40 mg of 10% is added and the mixture is hydrogenolysed at standard temperature and pressure for 1 hour in a hydrogen atmosphere. The mixture is diluted in $CH_2Cl_2$ and filtered on celite. The solvent evaporated to dryness and the residue is freeze-dried. White solid, 106 mg (60%).

ESI(+) [M+H]$^+$ mass=691.

1H NMR (DMSOd6) δ (ppm): 1.0-1.5 (24H m); 1.5-1.7 (2H m); 2.5 (2H m); 2.7-3.0 (3H m); 3.9 (1H m); 4.2 (1H m); 6.4 (1H m); 6.65 (1H m); 7.2-7.7 (9H+1H m); 8.3 (1H m).

Example 10

2-(4-bromo-benzyl)-acrylic acid benzyl ester

Step 1: 2-(4-bromo-benzyl)-acrylic acid

This compound is synthesised according to the protocol described for the synthesis of 2-Biphenyl-4-ylmethyl-acrylic acid (example 2), replacing biphenyl-4-yl-acetaldehyde by 4-bromo benzaldehyde. White solid.

HPLC ($CH_3CN$ (0.1% TFA)/$H_2O$ (0.1% TFA) 70:30, Kromasil C18 column) Rt=4.9 min.

Step 2: 2-(4-bromo-phenyl-4-ylmethyl-acrylic) acid benzyl ester

Esterification is performed according to the protocol described in step 3 of example 2. Colourless oil.

HPLC ($CH_3CN$ (0.1% TFA)/$H_2O$ (0.1% TFA) 70:30, Kromasil C18 column), Rt=22.0 min.

NMR (CDCl3) δ (ppm): 3.6 (2H s); 5.2 (2H s); 5.6 (1H d); 6.4 (1H d); 7.1 (2H d); 7.4 (7H m).

Example 11

2-(2-(4-bromo-benzyl)-3-{hydroxy-[1-(1-isobutyryloxy-ethoxycarbonylamino)-ethyl]-phosphinoyl}-propionylamino)-propionic acid benzyl ester

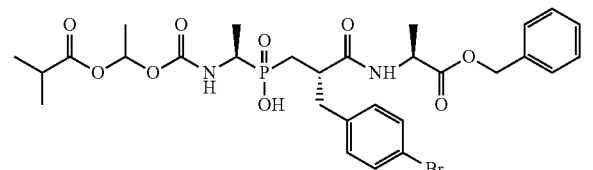

This compound is synthesised according to the protocol described for the synthesis of 2-biphenyl-4-ylmethyl-acrylic acid benzyl ester with 2-(4-bromo-benzyl)-acrylic acid benzyl ester.

Step 1: 3-[(1-benzyloxycarbonylamino-ethyl)-hydroxy-phosphinoyl]-2-(4-bromo-benzyl)-propionic acid benzyl ester The R configuration compound from example 1 (5.15 g) and the compound from example 10 (7.21 g) are placed in solution in BSA (18 ml) and the mixture is heated for 30 hours at 75° C. The reaction mixture is returned to ambient temperature and is diluted in ethyl acetate. The organic phase is washed with water and evaporated to dryness. A white solid product is obtained, corresponding to the mixture of the two 1R, 2S and 1R/2R diastereoisomers in relative proportions of 65:35. By recrystallisation from acetonitrile, the 1R, 2S isomer is obtained with an enantiomeric excess ee>97%. White solid, 3.35 g (42%).

NMR (DMSOd6) δ (ppm): 1.2 (3H dd); 1.7-2.2 (2H m); 2.7-3.1 (3H m); 3.8 (1H p); 4.95 (2H dd); 5.05 (2H s); 7.0-7.4 14H m); 7.55 (1H m).

Step 2: 3-((1-aminoethyl)-hydroxy-phosphinoyl)-2-(4-bromo-benzyl)-propionic acid Using 3.3 g of the compound from step 1 and according to the protocol described in step 2 of example 3, the expected compound in white solid form, 2.5 g (98%), is obtained.

Step 3: 2-(4-bromo-benzyl)-3-{hydroxy-[1-(1-isobutyryloxy-ethoxycarbonylamino)-ethyl]-phosphinoyl}-propionic acid Using 2.5 g of the compound from step 2 and according to the protocol described in step 3 of example 3, the expected compound is obtained. White solid, 2.6 g.

(M+H)$^+$ mass=508-510

NMR (DMSOd6) δ (ppm): 1.0-1.5 (12 Hm); 1.7 (2H m); 2.5 (1H m); 2.9 (3H m); 3.8 (1H) m); 6.6 (1H m); 7.1 (2H d); 7.4 (2H d); 7.75 (1H m).

Step 4: 2-(2-(4-bromo-benzyl)-3-{hydroxy-[1-(1-isobutyryloxy-ethoxycarbonylamino)-ethyl]-phosphinoyl}-propionylamino)-propionic acid benzyl ester Using 1 g of the compound from step 3 and 388 mg of alanine benzyl ester, the expected compound is obtained according to the protocol in step 4 of example 3. White solid.

(M+H)$^+$ mass=669-671

NMR (DMSOd6) δ (ppm): 1.0-1.3 (6H d); 1.25 (6H m); 1.45 (3H d); 1.6-1.9 (2H m); 2.5 (1H m); 2.7-3.0 (3H m); 3.7 (1H m); 4.3 (1H m); 5.0 2H dd)); 6.6 (1H m); 7.10 (2H d); 7.3 (4H s, +2H d); 7.5 (1H m), 8.4 (1H dd).

Example 12

2-(2-(4-bromo-benzyl)-3-{hydroxy-[1-(1-isobutyryloxy-ethoxycarbonylamino)-ethyl]-phosphinoyl}-propionylamino)-propionic acid

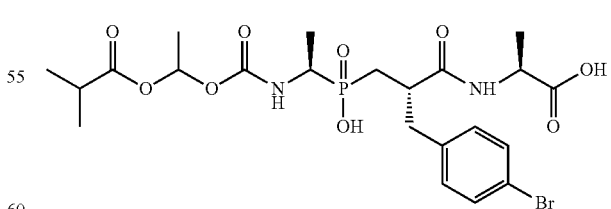

Step 1: 3-((1-benzoylcarbonylamino-ethyl)-hydroxy-phosphinoyl)-2-(4-bromo-benzyl)-propionic acid The compound from step 1 of example 11 (1.2 g) is solubilised in THF (10 ml) and 0.7 g of NaOH in solution in 5 ml of water is added. The mixture is stirred at ambient temperature for 3 hours. The THF is evaporated, the aqueous phase is acidified to pH=1 with a 1N HCl solution, and extracted with ethyl acetate. The organic phase is dried over $Na_2SO_4$, filtered and evaporated to dryness. White solid, 0.9 g (90%).

Step 2: 2-(3-((1-benzyloxycarbonylamino-ethyl)-hydroxy-phosphinoyl)-2-(4-bromo-benzyl)-propionylamino)-propionic acid t-butyl ester The compound from step 1 (0.9 g) is solubilised in 10 ml of DMF in nitrogen, and t-butyl alaninate hydrochloride (450 mg), 2.5 ml of DIEA (6 eq) and 1.98 g of TBTU (3 eq) are successively added. The mixture is stirred for 15 min at ambient temperature and the reaction is processed as in step 4 of example 3. 1.10 g of expected product (97%) is obtained.

Step 3: 2-(3-((1-amino-ethyl)-hydroxy-phosphinoyl)-2-(4-bromo-benzyl)-propionylamino)-propionic acid The compound obtained in step 2 is solubilised in a 50:50 $CH_2Cl_2$/TFA mixture (40 ml) and the mixture is stirred for 1 hour at ambient temperature. The residue is evaporated to dryness, taken up with water and freeze-dried. 1.0 g of the expected compound is obtained.

The compound is solubilised in an HBR/AcOH mixture (10 ml) and the solution is stirred for 1 hour at ambient temperature. The mixture is then evaporated at reduced pressure. The residue is taken up with water and freeze-dried. 930 mg of the expected product is obtained.

Step 4: 2-(2-(4-bromo-benzyl)-3-{hydroxy-[1-isobutyryloxy-ethoxycarbonylamino)-ethyl]-phosphinoyl}-propionylamino)-propionic acid The above compound is solubilised in 15 ml of $CH_2Cl_2$. 0.76 g of isobutyloxyethyl succinimidyl carbonate and 1.87 ml of DIEA are added and the mixture is stirred for 1 hour at ambient temperature. The mixture is then washed with $H_2O$ and with a saturated aqueous NaCl solution, dried over $Na_2SO_4$ and evaporated to dryness. The crude product is purified by HPLC.

HPLC (ACE C18 column, 40:60 $CH_3CH$ (0.1% TFA)/$H_2O$ (0.1% TFA) solvent) Rt 8.66 min.

ESI: (M+H)+=578-580

NMR (DMSO d6) δ (ppm): 1.0 (6H d); 1.1 (3H m); 1.2 (3H d); 1.35 (3H d); 1.6-1.9 (2H m); 2.5 (1H m); 2.7-2.9 (2H m); 3.7 (1H m); 4.1 (1H m); 6.6 (1H m); 7.1 (2H d); 7.4 (2H, d); 7.6 (1H dd); 8.2 (1H dd).

Example 13

(R)-benzyloxycarbonylamin)(thiophen-3-yl)methyl-phosphinic acid

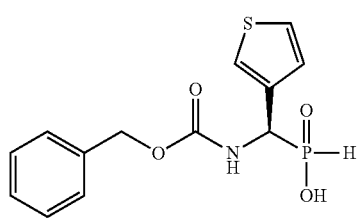 [SMILES: O=C(N[C@@H](c1ccsc1)[PH](=O)O)OCc1ccccc1]

Step 1: (Benzhydrylamino)(thiophen-3-yl)methyl-phosphinic acid

A mixture of 20.0 g (80 mmole) of diphenylmethylamine orthophosphate in 60 ml of anhydrous ethanol is boiled under reflux with stirring. 160.0 mmole of 3-Thiophene carboxaldehyde in solution in 19 ml of ethanol is added drop by drop in 30 min.

The reaction is followed by HPLC. After 2.5 hours, the reaction is returned to ambient temperature. An $Et_2O$/Acetone mixture (60 ml) is added to the mixture. The white precipitate obtained is filtered, washed with water (2×50 ml) and acetone (2×50 ml) and dried. White solid, 15.4 g (56%).

Step 2: Amino(thiophen-3-yl)methylphosphinic acid

A mixture of 15 g of the compound from step 1 and 122 ml of 6N HCl is boiled under reflux for 2 hours. After cooling, the reaction medium is concentrated by half and extracted with 3×1.5 l of ethyl ether. The solution is evaporated to dryness and the oily residue is taken up with 120 ml of ethanol. The solution is cooled to 0° C. and 30 ml of propylene oxide is added. A white solid precipitates. The precipitate is dewatered, washed with ethanol (2×20 ml), ethyl ether (2×10 ml) and dried. White solid, 7.32 g (95.1%).

(1H) NMR DMSO d6, δ (ppm): 4.92 (1H dd); 6.77 (1H, d); 7.10-7.50 (3H, m); 8.23 (3H m).

Step 3: (Benzyloxycarbonylamino)(thiophen-3-yl)methyl-phosphinic acid

The compound from step 2 is suspended in 25 ml of diaxane. The pH is adjusted to 9.5 by adding sodium hydroxide (23 ml). 6.46 ml of benzyl chloroformiate is added with stirring. After 3 hours at 0° C., the mixture is returned to ambient temperature and is poured onto a mixture of ice (1 L) and concentrated HCl (30 ml). The white precipitate formed is dewatered, washed with water (2×20 ml) and dried. White solid, 7.09 g (47%).

HPLC ($CH_3CN$ (0.1% TFA)/$H_2O$ (0.1% TFA) 70:30, Kromasil C18 column), Rt: 12.19 min.

The resolution of the racemic phosphinic acid is performed by recrystallising the salt obtained with the (R)(+) α-methyl-benzylamine, as described in Baylis et al. (J. Chem. Soc. Perkin Trans I 1984, 2845) in an ethyl acetate/isopropanol mixture=3.5:1. White solid, 1.42 g (27%).

(1H) NMR DMSO d6 δ (ppm): 4.92 (1H dd); 5.05 (2H, s); 6.77 (1H, d); 7.10-7.50 (8H, m); 8.20 (1H, d).

Example 14

(R)-(benzoylcarbonylamino)(phenyl)methyl-phosphinic acid

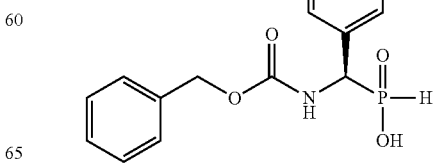

Step 1: (Benzhydrylamino)(phenyl)methylphosphinic acid

A mixture of 24.95 g (100 mmole) of diphenylmethylamine orthophosphate in 75 ml of anhydrous ethanol is boiled under reflux with stirring. 200 mmole of benzaldehyde in solution in 24 ml of ethanol is added drop by drop in 30 min. The reaction is followed by HPLC. After 2.5 hours, the reaction is returned to ambient temperature. An Et$_2$O/Acetone mixture (75 ml) is added to the mixture. The white precipitate obtained is filtered, washed with water (2×60 ml) and acetone (2×60 ml) and dried. White solid, 20.2 g (60.1%).

Step 2: Amino(phenyl)methylphosphinic acid

A mixture of 20 g of the compound from step 1 and 160 ml of 6N HCl is boiled under reflux for 2 hours. After cooling, the reaction medium is concentrated by half and extracted with 3×1.5 l of ethyl ether. The solution is evaporated to dryness and the oily residue is taken up with 160 ml of ethanol. The solution is cooled to 0° C. and 40 ml of propylene oxide is added. A white solid precipitates. The precipitate is dewatered, washed with ethanol (2×20 ml), ethyl ether (2×10 ml) and dried. White solid, 7.25 g (95.3%).

(1H) NMR DMSO d6 δ (ppm): 4.92 (1H dd); 6.77 (1H, d); 7.10-7.50 (5H, m); 8.23 (3H, m).

Step 3: (Benzyloxycarbonylamino)(phenyl)methyl-phosphinic acid

The compound from step 2 is suspended in 25 ml of diaxane. The pH is adjusted to 9.5 by adding sodium hydroxide (23 ml). 6.46 ml of benzyl chloroformate is added with stirring. After 3 hours at 0° C., the mixture is returned to ambient temperature and is poured onto a mixture of ice (1 L) and concentrated HCl (30 ml). The white precipitate formed is dewatered, washed with water (2×20 ml) and dried. White solid, 11.44 g (88.5%).

HPLC (CH$_3$CN (0.1% TFA)/H$_2$O (0.1% TFA) 40:60, Kromasil C18 column), Rt 3.90 min.

The resolution of the racemic phosphinic acid is performed by recrystallising the salt obtained with the (R)(+) α-methylbenzylamine, as described in Baylis et al. (J. Chem. Soc. Perkin Trans I 1984, 2845) in an ethyl acetate/isopropanol mixture=3.5:1. White solid, 3.9 g (34.0%).

(1H) NMR DMSO d6 δ (ppm): 4.92 (1H dd); 5.0 (2H, s); 6.77 (1H, d); 7.10-7.50 (8H, m); 8.31 (1H, d).

Example 15

2-(4-Thiophen-3-yl-benzyl)-acrylic acid methyl ester

This compound is synthesised according to the protocol described for the synthesis of 2-Biphenyl-4-ylmethyl-acrylic acid (example 2) by replacing biphenyl-4-yl-acetaldehyde by 4-bromo benzaldehyde. White solid (48.0%).

HPLC (CH$_3$CN (0.1% TFA)H$_2$O (0.1% TFA) 70:30, Kromasil C18 column) Rf=11.28 min.

Example 16

2-[2-{Hydroxy-[(1-isobutyryloxy-ethoxycarbonylamino)-phenyl-methyl]-phosphinoylmethyl}-3-(4-thiophen-3-yl-phenyl)-propionylamino]-propionic acid

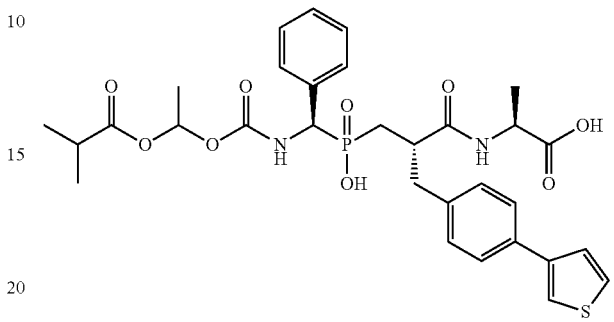

This compound is synthesised according to the protocol described in example 3 by replacing 2-biphenyl-4-ylmethyl-acrylic acid benzyl ester with 2-(4-thiophen-3-yl-benzyl)-acrylic acid methyl ester (example 15).

Step 1: 3-[(1-benzyloxycarbonylamino-ethyl)-hydroxy-phosphinoyl]-2-(4-Thiophen-3-yl-benzyl)-propionic acid ethyl ester The R configuration compound from example 14 (15.42 g; 1.2 eq) and the compound from example 15 (13.82 g; 1.0 eq) are placed in solution in BSA (50 ml) and the mixture is heated for 15 hours at 75° C. The reaction mixture is returned to ambient temperature and is diluted in ethyl acetate. The organic phase is washed with water and evaporated to dryness. A white solid product is obtained, corresponding to the mixture of the two 1R, 2S and 1R, 2R diastereoisomers in relative proportions of 65:35. White solid, 17.26 g (68%).

HPLC (CH$_3$CN (0.1% TFA)/H$_2$O (0.1% TFA) 70:30, Kromasil C18 column), Rt=6.51 min.

NMR (DMSOd6) δ (ppm): 1.50 (3H, t), 1.81-2.16 (2H, m); 2.78-3.12; (2H, m), 3.68 (3H, s); 3.78 (1H, qt); 4.50 (2H, q); 4.90 (1H, m); 5.20 (2H, s); 7.12-8.15 (17H arom. +NH, m).

Step 2: (R)-amino(phenyl)methyl-3-ethoxy-3-oxo-2-(4-thiophen-3-yl)benzyl)propyl)phosphinic acid ethyl ester hydrobromide 17.86 g of the compound from step 1 is solubilised in 180 ml of 48% HBr in AcOH. The mixture is stirred for 1 hour at ambient temperature and the mixture is evaporated at reduced pressure to produce the crude product in oil form (100%).

NMR (DMSOd6) δ (ppm): 1.50 (3H, t), 1.81-2.16 (2H, m); 2.78-3.12 (2H, m); 3.68 (3H, s); 3.78 (1H, qt); 4.50 (2H, q); 4.90 (1H, m); 5.20 (2H, s); 7.12-8.15 (12 H, m); 8.15 (3H, m).

Step 3: (R)-(tert-butoxycarbonylamino)(phenyl)methyl ((S)-3-ethoxy-3-oxo-2-(4-(thiophen-3-yl)benzyl)propyl) phosphinic acid ethyl ester The compound from step 2 (30.9 mmol) is solubilised in 300 ml of DMF. To this solution, Et$_3$N (35 ml, 250 mmol, 8 eq) and Boc$_2$O (6.75 g, 1 eq) in 50 ml of DMF. The mixture is stirred overnight at ambient temperature. The DMF is evaporated at reduced pressure and the mixture is taken up with EtoAc. The organic phase is washed with a 10% citric acid solution, a 10% NaHCO$_3$ solution, a sat. NaCl solution, dried over Na$_2$SO$_4$ and concentrated at reduced pressure to produce 15.16 g of product (90.2%).

HPLC (CH$_3$CN (0.1% TFA)/H$_2$O (0.1% TFA) 70:30, Kromasil C18 column), Rt=5.42 min.

NMR (DMSOd6) δ (ppm) 1.50 (3H, t); 1.45 (9H, s); 1.81-2.16 (2H, m); 2.78-3.12 (2H, m); 3.78 (1H, qt); 4.50 (2H, q); 4.90 (1H, m); 7.12-8.0 (12 H aromatic +NH, m).

Step 4: 3-(((R)-tert-butoxycarbonylamino) (phenyl) methyl) (hydroxy)phosphoryl)-2-(4-(thiophen-3-yl) benzyl) propanoic acid The compound from step 3 (15.16 g; 27.88 mmol) is solubilised in 280 ml of acetone and 1N NaOH (278.8 ml. 10 eq) is added drop by drop. The mixture is stirred overnight at ambient temperature and the acetone is evaporated at reduced pressure. The mixture is taken up with EtoAc. The aqueous phase is extracted and is acidified with 1N HCl. The aqueous phase is then extracted with EtoAc. The organic phase is then washed with H$_2$O, sat. NaCl, dried over Na$_2$SO$_4$ and evaporated at reduced pressure to produce 13.73 g of oil (95%).

HPLC (CH$_3$CN (0.1% TFA)/H$_2$O (0.1% TFA) 50:50, Kromasil C18 column), Rt=11.40 min.

NMR (DMSOd6) δ (ppm) 1.45 (9H, s); 1.81-2.16 (2H, m); 2.78-3.12, (2H, m); 3.78 (1H, qt); 4.90 (1H, m); 7.12-8.0 (12 H aromatic +NH, m).

Step 5: (R)-(tert-butoxycarbonylamino)(phenyl) (methyl((S)-3-((S)-1-methoxy-1-oxopropan-2-ylamino)-3-oxo-2-(4-(thiophen-3-yl)benzyl)propyl)phosphinic acid methyl ester Using 150 mg of the compound from step 4 and 52 mg of alanine methyl ester, the expected compound is obtained according to the protocol of step 4 of example 3.

The expected diastereoisomer is obtained by semi-preparative HPLC on a Kromasil C18 column with 50:50 CH$_3$CN (0.1% TFA)/H$_2$O (0.1% TFA) as the elution system. White solid: 50 mg (30.0%).

HPLC (CH$_3$CN (0.1% TFA)/H$_2$O (0.1% TFA) 70:30, Kromasil C18 column), Rt=6.0 min.

NMR (DMSOd6) δ (ppm): 1.10-1.50 (12H, m); 1.81-2.16 (2H, m); 2.78-3.12, (3H, m); 3.48 (3H, s); 3.78 (1H, qt); 4.25 (1H, d); 4.90 (1H, m); 7.12-7.81 (12 H+NH, m); 8.5 (1H, d).

Step 6: (R)-(tert-butoxycarbonylamino)(phenyl)methyl ((S)-3-((S)-1-methoxy-1-oxypropan-2-ylamino)-3-oxo-2-(4-(thiophen-3-yl)benzyl)propyl)phosphinic acid 50 mg of the compound from step 5 is placed in solution in 2 ml of acetone. 800 μl of 1N NaOH (10 eq) is added and the mixture is stirred for 2.5 hours at ambient temperature and the acetone is evaporated at reduced pressure. The mixture is taken up with EtoAc. The aqueous phase is extracted and is acidified with 1N HCl. The aqueous phase is then extracted with EtoAc. The organic phase is then washed with H$_2$O, sat. NaCl, dried over Na$_2$SO$_4$ and evaporated at reduced pressure to produce 48 mg (98%).

HPLC (CH$_3$CN (0.1% TFA)/H$_2$O (0.1% TFA) 50:50, Kromasil C18 column), Rt=7.91 min.

NMR (DMSOd6) δ (ppm): 1.10-1.50 (12H, m); 1.81-2.16 (2H, m); 2.78-3.12, (3H, m); 3.78 (1H, qt); 4.25 (1H, d); 4.90 (1H, m); 7.12-7.81 (12 H+NH, m); 8.5 (1H, d).

Step 7: (2S)-2-((2S)-3-(((R)-amino(phenyl)methyl) (hydroxy)phosphoryl)-2-(4-(thiophen-3-yl)benzyl) propanamido)propanoic acid trifluoroacetate 48 mg of the compound from step 6 is placed in solution in 4 ml of DCM. 60 μl of trifluoroacetic acid is added and the mixture is stirred for 45 min at 0° C. The mixture is evaporated at reduced pressure to produce 49 mg (100%).

HPLC (CH$_3$CN (0.1% TFA)/H$_2$O (0.1% TFA) 50:50, Kromasil C18 column) Rt=2.60 min.

NMR (DMSOd6) δ (ppm): 1.20 (3H, d); 1.81-2.16 (2H, m); 2.78-3.12, (3H, m); 3.78 1H (qt.); 4.25 (1H, d); 4.90 (1H, m); 7.12-7.81 (12H, m); 8.4 (1H, d); 8.7 (3H, m).

Step 8: 2-[2-{Hydroxy-[(1-isobutyryloxy-ethoxycarbonyl-amino)-phenyl-methyl]-phosphinoylmethyl}-3-(4-thiophen-3-yl-phenyl)-propionylamino]-propionic acid The above compound is solubilised in 1 ml of CH$_3$CN and 340 μl of 2N NaHCO$_3$ and 34 mg of isobutyloxyethyl succinimide carbonate (1.2 eq.) is added and the mixture is stirred for 1 hour at 60° C. The mixture is taken up with ethyl acetate and is washed with H$_2$O and with a saturated aqueous NaCl solution, dried over Na$_2$SO$_4$ and evaporated to dryness. The unprocessed product is purified with HPLC.

HPLC (CH$_3$CN (0.1% TFA)/H$_2$O (0.1% TFA) 38:62, Atlantis T3 column) Rt=10.52 min.

NMR (DMSOd6) δ (ppm): 1.0-1.3 (6H d); 1.20 (3H, d); 1.25 (3H, d); 1.81-2.16 (2H, m); 2.78-3.12, (3H, m); 3.78 1H (qt.); 4.25 (1H, d); 4.90 (1H, m); 6.64 (1H m); 7.12-7.81 (13H, m); 8.28 (1H, d).

Example 17

2-[2-{Hydroxy-[(1-isobutyryloxy-ethoxycarbony-lamino)-phenyl-methyl]-phosphinoylmethyl}-3-(4-thiophen-3-yl-phenyl)-propionylamino]-3-hydroxypropionic acid

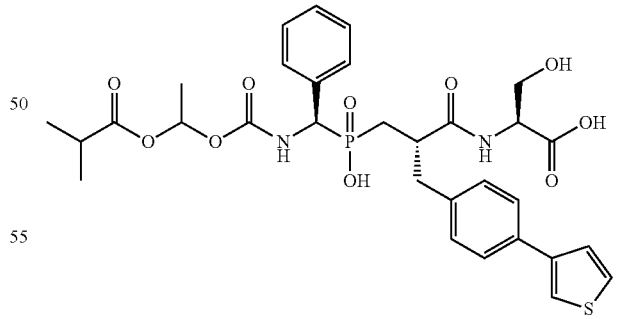

This compound is synthesised according to the protocol described in example 16 by replacing alanine methyl ester by serine methyl ester (O-tBu).

HPLC (CH$_3$CN (0.1% TFA)/H$_2$O (0.1% TFA) 38:62, Atlantis T3 column) Rt=10.02 min.

NMR (DMSOd6) δ (ppm): 1.0-1.3 (6H, d); 1.20 (3H, d); 1.81-2.16 (2H, m); 2.78-3.12, (3H, m); 3.40-3.60 (2H, m);

3.78 (1H, qt); 4.25 (1H, d); 4.90 (1H, m); 6.64 (1H m); 7.12-7.81 (13H, m); 8.28 (1H, d).

Example 18

2-(3-Biphenyl-4-yl-2-{hydroxy-[(1-isobutyryloxy-ethoxycarbonylamino)-thiophen-3-yl-methyl]-phosphinoylmethyl}-propionylamino)-propionic acid

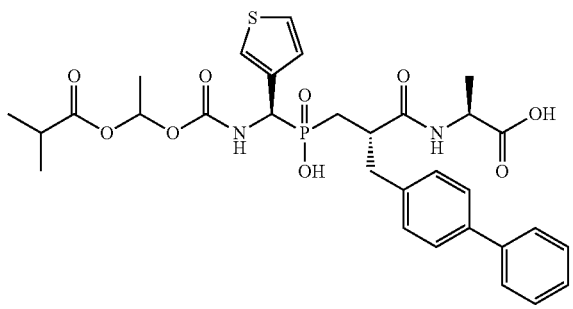 [SMILES: CC(OC(=O)N[C@@H](c1ccsc1)P(=O)(O)C[C@@H](Cc1ccc(-c2ccccc2)cc1)C(=O)N[C@@H](C)C(=O)O)OC(=O)C(C)C]

Step 1: 3-(((R)-(benzyloxycarbonylamino)(thiophen-3-yl)methyl)(hydroxy)phosphoryl)-2-(biphenyl-4-ylmethyl)propanoic The R configuration compound from example 13 (660 mg; 1.0 eq) and the compound from example 2 (642 mg; 1.2 eq) are placed in solution in BSA (5 ml) and the mixture is heated for 15 hours at 75° C. The reaction mixture is returned to ambient temperature and is diluted in ethyl acetate. The organic phase is washed with water and evaporated to dryness. A white solid product is obtained, corresponding to the mixture of the two 1R, 2S and 1R, 2R diastereoisomers in relative proportions of 65:35. White solid, 1.4 g (100%).

NMR (DMSOd6) δ (ppm): 1.60-2.00 (2H, m); 2.78-3.12, (2H, m); 3.78 (1H, qt); 4.90 (1H, m); 5.20 (2H, s); 7.12-8.5 (17 H arom. +NH, m).

Step 2: (R)-(benzyloxycarbonylamino)(thiophen-3-yl)methyl(2-(biphenyl-4-ylmethyl)-3-((S)-1-methoxy-1-oxopropan-2-ylamino)-3-oxopropyl)phosphinic acid Using 2.12 mmol of the compound from step 1 and 2.75 mmol of alanine methyl ester, the expected compound is obtained according to the protocol of step 4 of example 3. White solid: 1.40 g (90.0%).

NMR (DMSOd6) δ (ppm): 1.25-1.40 (3H, m); 1.60-2.00 (2H, m); 2.78-3.12, (2H, m); 3.40 (3H; s); 3.78 (1H, qt); 4.25 (1H, m); 4.90 (1H, m); 5.20 (2H, s); 7.12-8.15 (17 H arom. +NH, m).

Step 3: 2-{2-[(Benzyloxycarbonylamino-thiophen-3-yl-methyl)-hydroxy-phosphinoylmethyl]-3-biphenyl-4-yl-propionylamino}-propionic acid 100 mg of the compound from step 2 is placed in solution in 4 ml of acetone. 1.6 ml of 1N NaOH (10 eq) is added and the mixture is stirred for 2.5 hours at ambient temperature and the acetone is evaporated at reduced pressure. The mixture is taken up with EtoAc. The aqueous phase is extracted and is acidified with 1N HCl. The aqueous phase is then extracted with EtoAc. The organic phase is then washed with H₂O, sat. NaCl, dried over Na₂SO₄ and evaporated at reduced pressure to produce 98 mg (98%).

NMR (DMSOd6) δ (ppm): 1.25-1.40 (3H, m); 1.60-2.00 (2H, m); 2.78-3.12, (2H, m); 3.78 (1H, qt); 4.25 (1H, m); 4.90 (1H, m); 5.20 (2H, s); 7.12-8.15 (17 h arom. +NH, m).

Step 4: (2S)-2-((2S)-3-(((R)-amino(thiophen-3-yl)methyl)(hydroxy)phosphoryl)-2-(biphenyl-4-ylmethyl) propanamido)propanoic acid trifluoroacetate The compound from step 3 is placed in solution in 4 ml of 48% HBr in solution in acetic acid. The mixture is stirred for 2 hours at ambient temperature. The mixture is evaporated at reduced pressure and the residue is purified by semi-preparative HPLC on a Kromasil C18 column with 50:50 CH₃CH (0.1% TFA)/H₂O (0.1% TFA) as the elution system. White solid: 28 mg (57.1%).

NMR (DMSOd6) δ (ppm): 1.25-1.40 (3H, m); 1.60-2.00 (2H, m); 2.78-3.12, (2H, m); 3.78 (1H, qt); 4.25 (1H, m); 4.90 (1H, m); 7.12-8.15 (12 H, m); 8.50 (3H, m).

Step 5: 2-(3-Biphenyl-4-yl-2-{hydroxy-{(1-isobutyryloxy-ethoxycarbonylamino)-thiophen-3-yl-methyl]-phosphinoylmethyl}-propionylamino)-propionic acid The above compound is solubilised in 1 ml of CH₃CN and 195 µl of 2N NaHCO₃ and 20 mg of isobutyloxyethyl succinimide carbonate (1.2 eq.) is added. The mixture is stirred for 1 hour at 60° C. The mixture is taken up with ethyl acetate and is washed with H₂O and with a saturated aqueous NaCl solution, dried over Na₂SO₄ and evaporated to dryness. The crude product is purified with HPLC.

HPLC (CH₃CN (0.1% TFA)/H₂O (0.1% TFA) 38:62, Atlantis T3 column) Rt=10.42 min.

NMR (DMSOd6) δ (ppm): 1.0-1.3 (6H d); 1.20 (3H, d); 1.25 (3H, d); 1.80-2.20 (2H, m); 2.80-3.20, (3H, m); 3.75 1H (qt.); 4.25 (1H, d); 4.90 (1H, m); 6.65 (1H m); 7.10-7.80 (13H, m); 8.28 (1H, d).

Example 19

2-{3-Biphenyl-4-yl-2-[hydroxy-(1-isobutyryloxymethoxy carbonylamino-ethyl)-phosphinoylmethyl]-propionylamin}-propionic acid

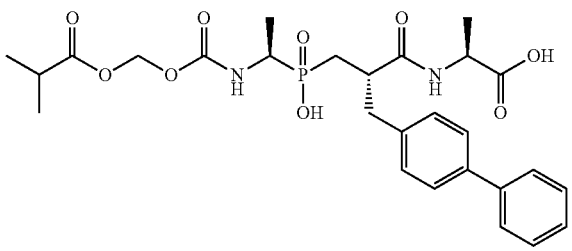 [SMILES: CC(C)C(=O)OCOC(=O)N[C@@H](C)P(=O)(O)C[C@@H](Cc1ccc(-c2ccccc2)cc1)C(=O)N[C@@H](C)C(=O)O]

Step 1: 2-[(1-Benzyloxycarbonylamino-ethyl)-hydroxy-phosphinoylmethyl]-3-biphenyl-4-yl-propionic acid The compound from step 1 of example 3 (1.2 g) is solubilised in THF (10 ml) and 0.7 g of NaOH in solution in 5 ml of water is added. The mixture is stirred at ambient temperature for 3 hours. The THF is evaporated, the aqueous phase is acidified to pH 1 with 1N HCl, and extracted with ethyl acetate. The organic phase is dried over $Na_2SO_4$, filtered and evaporated to dryness. White solid, 0.9 g (90%).

HPLC ($CH_3CN$ (0.1% TFA)/$H_2O$ (0.1% TFA) 38:62, ACE C18 column) Rt=17.16 min.

1H NMR (DMSOd6): δ (ppm) 1.26 (3H, dd); 1.81-2.16 (2H, m); 2.78-3.12 (3H, m); 3.78 (1H, qt); 5.20 (2H, q); 7.12-7.68 (14H arom. +NH (m).)

Step 2: 2-{2-[(1-Benzyloxycarbonylamino-ethyl)-hydroxy-phosphinoylmethyl]-3-biphenyl-4-yl-propionylamino}-propionic acid t-butyl ester The compound from step 1 (0.9 g) is solubilised in 10 ml of DMF in nitrogen, and t-butyl alaninate hydrochloride (450 mg), 2.5 ml of DIEA (6 eq) and 1.98 g of TBTU (3 eq) are successively added. The mixture is stirred for 15 min at ambient temperature and the reaction is processed as in step 4 of example 3. 1.10 g of expected product (97%) is obtained.

HPLC ($CH_3CN$ (0.1% TFA)/$H_2O$ (0.1% TFA) 50:50, ACE C18 column) Rt=11.93 min.

NMR (DMSO d6): δ (ppm) 1.15-1.35 (6H, m); 1.42 (9H, s); 1.81-2.16 (2H, m); 2.78-3.12 (3H, m); 3.78 (1H, qt); 4.22 (1H, q); 5.20 (2H, q); 7.12-7.68 (14H arom. +NH (m).

Step 3: 2 (2S)-2-((2S)-3-(((R)-1-aminoethyl) (hydroxy) phosphoryl)-2-(biphenyl-4-ylmethyl)propanamido) propanoic acid The compound obtained in step 2 is solubilised in an HBr/AcOH mixture (10 ml) and the solution is stirred for 1 hour at ambient temperature. The mixture is then evaporated at reduced pressure. The residue is taken up with water and freeze-dried. 930 mg of the expected compound is obtained (100%).

HPLC ($CH_3CN$ (0.1% TFA)/$H_2O$ (0.1% TFA) 50:50, ACE C18 column) Rt=11.93 min.

1H NMR (DMSOd6): δ (ppm) 1.15-1.35 (6H, m), 1.42 (9H, s), 1.81-2.16 (2H, m), 2.78-3.12 (3H, m), 3.78 (1H, qt), 4.22 (1H, q), 5.20 (2H, q), 7.12-7.68 (14H arom. +NH (m).

Step 4: 2-{3-Biphenyl-4-yl-2-[hydroxy-(1-isobutyryloxy-methoxy carbonylamino-ethyl)-phosphinoylmethyl]-propionylamino}-propionic acid 300 mg of the compound from step 3 is solubilised in 2 ml of $CH_3CN$ and 2 ml of 2N $NaHCO_3$ and 186 mg of isobutyloxyethyl succinimide carbonate (1.2 eq.) is added. The mixture is stirred for 1 hour at 60° C. The mixture is taken up with ethyl acetate and is washed with $H_2O$ and with a saturated aqueous NaCl solution, dried over $Na_2SO_4$ and evaporated to dryness. The crude product is purified by HPLC to produce 170 mg of the desired product (50.5%).

HPLC ($CH_3CN$ (0.1% TFA)/$H_2O$ (0.1% TFA) 38:62, Atlantis T3 column) Rt=8.15 min.

NMR (DMSOd6) δ (ppm): 1.0-1.3 (6H d); 1.25 (3H, dd); 1.45 (3H, d); 1.6-1.9 (2H, m); 2.5 (1H, m); 2.7-3.0 (3H, m); 3.7 (1H, m); 4.3 (1H, m); 5.65 (2H, s); 7.10-7.80 (9H, m); 8.4 (1H dd).

Example 20

2-Dimethyl-propionic acid 1-(1-{[3-biphenyl-4-yl-4-yl-2-(1-carboxy-ethylcarbamoyl)-propyl]-hydroxy-phosphinoyl}-ethylcarbamoyloxy)-ethyl acid

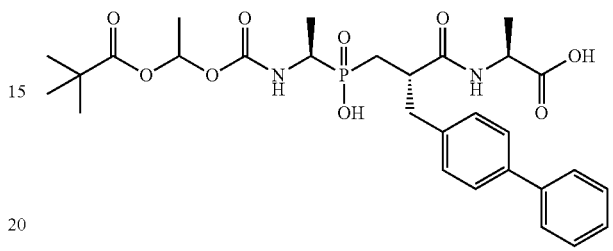

394 mg of the compound from step 3, example 19 is solubilised in 2 ml of $CH_3CN$ and 2 ml of 2N $NaHCO_3$ and 272 mg of isobutyloxyethyl succinimide carbonate (1.2 eq.) is added and the mixture is stirred for 1 hour at 60° C. The mixture is taken up with ethyl acetate and is washed with $H_2O$ and with a saturated aqueous NaCl solution, dried over $Na_2SO_4$ and evaporated to dryness. The crude product is purified by HPLC to produce 330 mg of the desired product (71.6%).

HPLC ($CH_3CN$ (0.1% TFA)/$H_2O$ (0.1% TFA) 38:62, Atlantis T3 column) Rt=16.93 and 18.41 min.

NMR (DMSOd6) δ (ppm): 1.20 (9H, d); 1.25 (3H, dd); 1.45 (3H, d); 1.6-1.9 (2H, m); 2.5 (1H, m); 2.7-3.0 (3H, m); 3.7 (1H, m); 4.3 (1H, m); 6.6 (1H, m); 7.10-7.80 (9H, m); 8.4 (1H dd).

Example 21

2-[(1-{Hydroxy-[1-(1-isobutyryloxy-ethoxycarbonylamino)-ethyl]-phosphinoylmethyl}-cyclopentanecarbonyl)-amino]-propionic acid

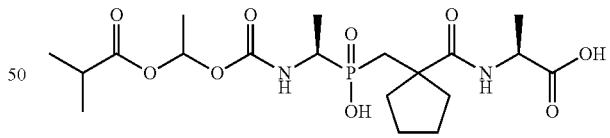

Step 1: cyclopentanoic acid t-butyl ester

Cyclopentanoic acid (15 g, 0.131 mol), tBuOH (2.1 ml) and $H_2SO_4$ (750 µl) are placed in a thick-walled flask. Approximately 150 ml condensed isobutylene at −78° C. is then added. The flask is sealed, allowed to return to ambient temperature and stirred for 4 nights at ambient temperature.

After evaporating the excess isobutylene, the mixture is taken up which $Et_2O$ and washed with 10% $NaHCO_3$. The organic phase is dried over $Na_2SO_4$ and concentrated at reduced pressure to produce 12.03 g of the expected product (yield: 80.6%).

NMR (CDCl3) δ (ppm): 1.40 (9H, d); 1.45-1.90 (8H, m); 2.55 (1H, m).

Step 2: 1-(hydroxymethyl)cyclopentanecarboxylic acid t-butyl ester

To a solution at 0° C. of iPR$_2$NH (7.91 ml, 56.11 mmol) in THF (190 ml), nBuLi in hexane (2.5 M, 23.3 ml, 58.17 mmol, 1.04 eq) is added. After 30 min, the mixture is cooled to −78° C. and a solution of the compound from step 1 (9.54 g, 56.11 mmol) in 25 ml of THF is added in nitrogen in 30 min. The mixture is stirred for 1 hour at −78° C. and paraformaldehyde (5 eq, 8.37 g) is added and the mixture is stirred for 1 hour at −78° C. and for 12 hours at ambient temperature.

190 ml of a sat. NH$_4$Cl solution is added and the mixture is extracted with EtoAc (2×200 ml). The organic phase is washed with 1N HCl, sat. NaCl, dried over Na$_2$SO$_4$ and concentrated at reduced pressure to produce the desired product (yield: 60%).

NMR (CDCl$_3$) δ (ppm): 1.40 (9H, d); 1.45-1.90 (8H, m); 3.50 (2H, s).

HPLC Atlantis T3 4.6×100 mm, 3 µm, gradient: CH$_3$CN (0.1% TFA)/H$_2$O (0.1% TFA) 10 to 90% CH$_3$CN in 30 min, Rt: 12.43 min.

Step 3: Benzyl (1R)-1-(methoxyhydrophosphoryl)ethylcarbamate

Under nitrogen, the compound from step 2, example 3 (6 g, 24.67 mmol) is solubilised in a MeOH/Toluene mixture. A trimethylsilyldiazomethane solution is added drop by drop until the colour persists (corresponding to the end of the gas emission). The mixture is stirred for 1 hour at ambient temperature and the toluene is evaporated at reduced pressure. The mixture is extracted with EtoAc. The organic phase is washed with 10% NaHCO$_3$, sat. NaCl, dried over Na$_2$SO$_4$ and concentrated at reduced pressure to produce 5.75 g of desired product (yield 90.7%).

NMR (DMSO d6) δ (ppm): 1.20-1.35 (3H, m); 3.60 (2H, m); 3.70-4.10 (1H, m); 5.05 (2H, d); 6.90 (1H, m); 7.20-7.50 (5H, m); 7.75 (1H, m).

HPLC Atlantis T3 4.6×100 mm, 3 µm, CH$_3$CN (0.1% TFA)/H$_2$O (0.1% TFA) 30 to CH$_3$CN in 30 min, Rt: 4.30 and 4.48 min.

Step 4: 1-((trifluoromethylsulfonyloxy)methyl)cyclopentanoic tert-butyl ester A mixture of 6.80 ml (84.2 mmol) of pyridine and of 50 ml of dichloromethane is cooled to −78° C. in nitrogen. A triflic anhydride solution, 6.80 g (24.14 mmol) in 7 ml of CH$_2$Cl$_2$ is added using a bromine vial. After 10 min, a solution of 3.4 g of the compound from step 2 (17 mmol) in 14 ml of CH$_2$Cl$_2$ is added drop by drop. The mixture is stirred for 30 min at −78° C. and is returned to ambient temperature. 300 ml of hexane is added. The organic phase is washed with 1N NaOH, H$_2$O, sat. NaCl, dried over Na$_2$SO$_4$ and concentrated at reduced pressure to produce 5.67 g of desired product (yield: 100%) used as it is for the next step.

NMR (CDCl$_3$) δ (ppm): 1.40 (9H, d); 1.45-1.90 (8H, m); 4.65 (2H, s).

Step 5: 1((((R)-1-benzyloxycarbonylamino)ethyl) (hydroxy)phosphoryl)methyl)cyclopentane carboxylic acid A solution of iPr$_2$NH (2.19 ml, 15.64 mmol) in THF (17 ml) is cooled to 0° C. and 6.23 ml of 2.5 M nBuLi in hexane (15.64 mmol, 1.04 eq) is added. After 15 min, the mixture is cooled to −78° C. and a solution of the compound from step 3 (3.64 g, 14.16 mmol) in 28 ml of THF is added under nitrogen to keep the temperature below −60° C. The mixture is stirred for 10 min at −78° C. and the compound from step 4 (17 mmol) is added in 15 ml of THF and the mixture is stirred for 15 min at −78° C. and for 4 hours at ambient temperature.

The mixture is diluted with EtoAc. The organic phase is washed with 1N HCl, 10% NaHCO$_3$, sat. NaCl, dried over Na$_2$SO$_4$ and concentrated at reduced pressure.

The crude product obtained is placed in solution in 10 ml of CH$_2$Cl$_2$ and 3.2 ml of TFA is added. The mixture is stirred for 2 hours at 0° C. After evaporating to dryness, the expected product is purified by semi-preparative HPLC on an ACE C18 column, CH$_3$CN (0.1% TFA)/H$_2$O (0.1% TFA) 40:60 to produce 120 mg of pure product (yield: 29.4%).

NMR (DMSO d6) δ )ppm): 1.20-1.35 (3H, m); 1.50-2.20 (10H, m); 3.75 (1H, q); 5.05 (2H, d); 5.05 (2H, d); 7.20-7.60 (6H, m).

HPLC ACE C18 4.6×250 mm, 5 µm, CH$_3$CN (0.1% TFA)/H$_2$O (0.1% TFA) 40:60, Rt: 5.57 min.

Step 6: (R)-1-(benzyloxycarbonylamino)ethyl((1-(S)-1-tert-butoxy-1-oxypropan-2-ylcarbamoyl)cyclopentyl)methyl)phosphinic acid The compound from step 5 (0.118 g, 0.319 mmol) is solubilised in 2 ml of DMF under nitrogen, and t-butyl alaninate hydrochloride (70 mg), 279 µl of DIEA (5 eq) and 308 g of TBTU (3 eq) are successively added. The mixture is stirred for 15 min at ambient temperature, and the reaction is processed as in step 4 of example 3. 111 mg of the expected product is obtained (70.3%).

HPLC (CH$_3$CN (0.1% TFA)/H$_2$O (0.1% TFA) 50:50, ACE (C18) column) Rt: 7.71 min.

1H NMR (DMSOd6) δ (ppm): 1.15-1.35 (6H, m); 1.42 (9H, s); 1.40-2.20 (10H, m); 3.85 (1H, q); 4.15 (1H, q); 5.05 (2H, s); 7.1-7.45 (5H, m); 7.90 (1H, d).

Step 7: (2S)-2-(1-((((R)-1-aminoethyl) (hydroxy) phosphoryl methyl)cyclopentanecarboxamido) propanoic acid trifluoroacetate The compound obtained in step 6 is solubilised in an HBr/AcOH mixture (2 ml) and the solution is stirred for 1 hour at ambient temperature. The mixture is then evaporated at reduced pressure. The product is purified by semi-preparative HPLC on an ACE C18 column with a gradient of 0 to 60% CH$_3$CN in 30 min of a CH$_3$CN (0.1% TFA)/H$_2$O (0.1% TFA) mixture to produce 57.2 mg of the expected product (yield: 61.9%).

HPLC ACE C18 gradient: 0 to 60% CH$_3$CN in 30 min of a CH$_3$CN (0.1% TFA)/H$_2$O (0.1% TFA) mixture Rt: 9.97 min.

1H NMR (DMSOd6) δ (ppm): 1.15-1.35 (6H, m); 1.50-2.20 (10H, m); 3.40 (1H, q); 4.25 (1H, q); 7.85 (1H, d); 8.10 (3H, m).

Step 8: 2-[-(1-{Hydroxy-[1-(1-isobutyryloxy-ethoxycarbonylamino)-ethyl]-phosphinoylmethyl}-cyclopentane carbonyl)-amino]-propionic acid 55 mg of the compound from step 7 is solubilised in 1 ml of CH$_3$CN and 366 µl of 2N NaHCO$_3$. 35 mg of isobutyloxy succinimide carbonate (1.2 eq.) is added.

The mixture is stirred for 1 hour at 60° C. The mixture is taken up with ethyl acetate and is washed with H$_2$O and with a saturated aqueous NaCl solution, dried over Na$_2$SO$_4$ and evaporated to dryness. The unprocessed product is purified by HPLC to produce 45 mg of the desired product (71.4%).

HPLC ACE C18 CH$_3$CN (0.1%)/H$_2$O (0.1% TFA) 70:30 Rt=4.53 min.

1H NMR (DMSOd6) δ (ppm): 1.10-2.20 (19H, m); 3.40 (1H, q); 3.7 (1H, m); 4.25 (1H, q); 6.20 (m, 1H); 7.85 (1H, d); 8.4 (1H, dd)

Example 22

2-[(1-Acetyl-4-{Hydroxy-[1-(1-isobutyryloxy-ethoxycarbonylamino)-ethyl]-phosphinoyl-methyl}-piperidine-4-carbonyl)-amino]-propionic acid

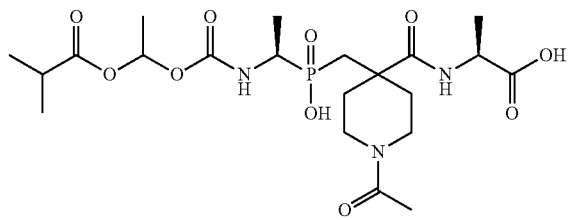 [SMILES: CC(=O)N1CCC(CP(=O)(O)[C@H](C)NC(=O)OC(C)OC(=O)C(C)C)(C(=O)N[C@@H](C)C(=O)O)CC1]

Step 1: 1-Acetyl-piperidine-4-carboxylic acid t-butyl ester 1-acetylpiperidine-4-carboxylic acid (2.97 g), suspended in 25 ml of a THF/toluene mixture and heated to 85° C. in a nitrogen stream. N,N dimethylformamide di-t-butyl acetal (25 ml, 6 eq) is added drop by drop and heating is maintained for 30 min. The mixture is evaporated to dryness and the residue is taken up with ethyl acetate. The organic phase is washed with water, with a saturated NaCl solution, dried over Na$_2$SO$_4$, filtered and evaporated to dryness. Yellow oil p=3.45 g (yield 88%).

HPLC Atlantis T3 10-90 gradient of CH$_3$CN (0.1% TFA/H$_2$O (0.1% TFA) in 15 min Rt=10.3 min.

ESI (+) (M+H)$^+$=228

NMR (DMSO d6) δ (ppm): 1.20-1.80 (13H, m), 2.10 (3H, s), 2.40 (1H, m). 2.60-3.20 (4H, m), 3.60-4.30 (4H, m).

Step 2: 1-Acetyl-4-hydroxymethyl-piperidine-4-carboxylic acid t-butyl ester

To a solution at 0° C. of iPR$_2$NH (2.10 ml, 14.89 mmol) in THF (16 ml), nBuLi in hexane (2.5 M) (6.8 ml, 16.92 mmol, 2.5 eq) is added. After 30 min, the mixture is cooled to −78° C. and a solution of the compound from step 1 (1.54 g, 6.77 mmol) in 9 ml of THF is added under nitrogen in 30 min. The mixture is stirred for 1 hour at −78° C. and paraformaldehyde (5 eq, 1.01 g) is added and the reaction mixture returned to ambient temperature with stirring. After 30 min at AT, the mixture is split between a saturated NH$_4$Cl (120 ml) and EtoAc (60 ml) solution. The aqueous phase is extracted with EtoAc (2×40 ml). The organic phase is washed with 1N HCl, sat. NaCl, dried over Na$_2$SO$_4$ and concentrated at reduced pressure to produce a yellow oil P=1.20 g.

The crude product is purified by semi-preparative HPLC on a 30×100 mm Atlantis column, CH$_3$CN (0.1% TFA)/H$_2$O (0.1% TFA) 15:85 eluent. Yield: 27%.

HPLC Atlantis T3 20% for 10 min followed by 20-90 gradient of CH$_3$CN (0.01% TFA)/H$_2$O (0.01% TFA) in 15 min Rt=8.85 min.

ESI (+) (M+H)$^+$=258.2

NMR (DMSO d6) δ (ppm): 1.20-1.80 (13H, m), 2.10 (3H, s), 2.60-3.20 (4H, m), 3.40 (2H, s), 3.60-4.30 (4H, m).

Step 3: 1-Acetyl-4-trifluoromethanesulfonyloxymethyl-piperidine-4-carboxylic acid tert-butyl ester A mixture of 2.0 ml (250 mmol) of pyridine and of 20 ml of dichloromethane is cooled to −78° C. under nitrogen. Triflic anhydride (2.10 ml, 12.5 mmol) is added drop by drop. After 10 min, a solution of 1.29 g of the compound from step 2 (5.0 mmol) in 15 ml of CH$_2$Cl$_2$ is added drop by drop. The mixture is stirred for 2 hours at −78° C. The organic phase is washed with 1N HCl, H$_2$O, sat. NaCl, dried over Na$_2$SO$_4$ and concentrated at reduced pressure to produce 1.68 g of the expected product (yield: 86%) used as it is for the next step.

HPLC Atlantis T3 (4.6*100 mm, 3 μm) 20% for 10 min followed by 20-90% gradient of CH$_3$CN (0.1% TFA/H$_2$O (0.1% TFA) in 15 min Rt=22.7 min.

ESI (+) (M+H)$^+$=390.2

NMR (CDCl$_3$) δ (ppm): 1.40-1.60 (11H, m), 1.90-2.30 (5H, m), 2.90 (2H, m), 3.40-3.80 (2H, m), 4.30-4.60 (2H, m).

Step 4: 1-acetyl-4-((((R)-1-(benzyloxycarbonylamino) ethyl) (hydroxy)phosphoryl)methyl)piperidine-4-carboxylic acid A solution of iPr$_2$NH (0.61 ml, 4.31 mmol) in THF (5 ml) is cooled to 0° C. and 3.1 ml of 1.5 M nBuLi in hexane (4.67 mmol, 3.0 eq) is added. After 15 min, the mixture is cooled to −78° C. and a solution of the compound from step 3 (925 mg, 3.59 mmol) in 8 ml of THF is added under nitrogen to keep the temperature below −60° C. The mixture is stirred for 10 min at −78° C. and the compound from step 4 (4.31 mmol) is added in 10 ml of THF and the mixture is stirred for 10 min at −78° C. and for 5 hours at ambient temperature.

The mixture is diluted with EtoAc. The organic phase is washed with 1N HCl, 10% NaHCO$_3$, sat. NaCl, dried over Na$_2$SO$_4$ and concentrated at reduced pressure. The crude product obtained is placed in solution in 31 ml of CH$_2$Cl$_2$ and 12 ml of TFA is added. The mixture is stirred for 2 hours at ambient temperature. After evaporating to dryness, the expected product is purified by semi-preparative HPLC on an Atlantis T3 column, CH$_3$CN (0.1% TFA)/H$_2$O (0.1% TFA) 15:85 to produce 367 mg of pure product (yield: 23%).

NMR (DMSO d6) δ (ppm): 1.17 (3H, m), 1.40-1.95 (9H, m), 3.00 (1H, m), 3.23 (1H, m), 3.55-3.81 (2H, m), 5.03 (dd, 2H), 7.33 (5H, m), 7.46 (1H, d).

HPLC Atlantic T3 4.6×100 mm, 3 μm, CH$_3$CN (0.1% TFA)/H$_2$O (0.1% TFA) 20:80, Rt: 7.67 min.

Step 5: (2S)-2-(1-acetyl-4-((((R)-1-aminoethyl) (hydroxy)phosphoryl)methyl)piperidine-4-carboxamide) propanoic acid trifluoroacetate The compound from step 4 (0.175 g, 0.41 mmol) is solubilised in 2 ml of DMF under nitrogen, and t-butyl alaninate hydrochloride (89 mg, 1.2 eq), 360 μl of DIEA (5 eq) and 395 mg of TBTU (3 eq) are successively added. The mixture is stirred for 15 min at ambient temperature, and the reaction mixture is evaporated to dryness. The crude residue obtained is solubilised in an HBr/AcOH mixture (4 ml) and the solution is then stirred for 1 hour at ambient temperature. The mixture is then evaporated at reduced pressure. The product is purified by semi-preparative HPLC on an Atlantis T3 column with a 0 to 30% gradient of CH$_3$CN in 30 min of a CH$_3$CN (0.1% TFA)/H$_2$O (0.1% TFA) mixture to produce 80.8 mg of the expected product (yield: 40.9%).

HPLC Atlantis T3 with a 0 to 30% gradient of CH$_3$CN in 30 min Rt: 8.59 min.

1H NMR (DMSOd6) δ (ppm): 1.15-1.35 (9H, m), 1.50-2.20 (10H, m), 3.23 (1H, m), 3.40 (1H, q), 4.25 (1H, q), 7.85 (1H, d), 8.10 (3H, m).

Step 6: 2-[(1-Acetyl-4-{Hydroxy-[1-(1-isobutyryloxy-ethoxycarbonylamino)-ethyl]-phosphinoylmethyl}-piperidine-4-carbonyl)-amino]-propionic acid 80 mg (0.166 mmol) of the compound from step 5 is solubilised in 2 ml of $CH_3CN$ and 560 μl of 2N $NaHCO_3$. 52 mg of isobutyloxy succinimide carbonate (1.2 eq.) is added and the mixture is stirred for 1 hour at 60° C. The mixture is taken up with ethyl acetate, washed with $H_2O$ and with a saturated aqueous NaCl solution, dried over $Na_2SO_4$ and evaporated to dryness. The crude product is purified with HPLC to produce 70 mg of the expected product (81.4%).

HPLC ACE C18 $CH_3CN$ (0.01%)/$H_2O$ (0.1% TFA) 50:50 Rt: 5.37 min.

1H NMR (DMSOd6) δ (ppm); 1.10-2.20 (29H, m), 3.20 (1H, m), 3.40 (1H, q), 3.7 (1H, m), 4.25 (1H, q), 6.20 (m, 1H), 7.85 (1H, d), 8.10 (3H, m).

Summary of the Molecules Described

This list is not exhaustive.

Example 23

Study of the Stability of Phosphinic Derivatives Protected with an Acyloxyalkyl Group on the Phosphinic Function and in which the Amine Function is Free The inhibition of neprilysin (NEP) and aminopeptidase N (APN) which is required to protect enkephalins completely from the catabolism thereof requires the recognition of the active sites of both zinc metallopeptidases by the same molecule in the present invention. This was obtained, in the prior art, with phosphinic derivatives particularly described in patent application FR 2 755 135. However, for parenteral route bioavailability reasons, it is necessary to protect the phosphinic function temporarily with an acylalkyl group (pro-drug) and, in some cases also the carboxyl function of the inhibitors described in the prior art.

Moreover, it is essential to note that the recognition of APN and the inhibition thereof necessarily requires the presence of a free amine function.

However, the study in solution of the pro-drugs described in the prior art demonstrates that protection of the phosphinic group by an acyloxyalkyl residue gives rise to the transfer of a part of this group to the amine function to produce a molecule having an amide function instead of the free amine necessary for APN affinity.

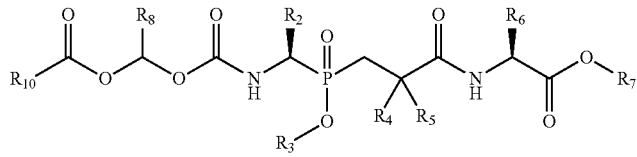

| Example | $R_{10}$ | $R_8$ | $R_3$ | $R_2$ | $R_4$ | $R_5$ | $R_6$ | $R_7$ |
|---|---|---|---|---|---|---|---|---|
| 3 | iPr | $CH_3$ | H | (R)—$CH_3$ | (S)-4-Phenyl—Benzyl | H | $CH_3$ | $CH_2Ph$ |
| 4 | iPr | $CH_3$ | H | (R)—$CH_3$ | (S)-4-Phenyl—Benzyl | H | $CH_3$ | H |
| 6 | iPr | $CH_3$ | H | (R)—$CH_3$ | (S)-4-Phenyl—Benzyl | H | $CH_3$ | $C_2H_5$ |
| 8 | iPr | $CH_3$ | H | (R)—$CH_3$ | (S)-4-Phenyl—Benzyl | H | $CH_3$ | $CH(CH_3)OCOOEt$ |
| 9 | iPr | $CH_3$ | $CH(CH_3)OCOiPr$ | (R)—$CH_3$ | (S)-4-Phenyl—Benzyl | H | $CH_3$ | H |
| 11 | iPr | $CH_3$ | H | (R)—$CH_3$ | (S)-4-Bromo-Benzyl | H | $CH_3$ | $CH_2Ph$ |
| 12 | iPr | $CH_3$ | H | (R)—$CH_3$ | (S)-4-Bromo—Benzyl | H | $CH_3$ | H |
| 16 | iPr | $CH_3$ | H | (R)—Phenyl | (S)-4-(3-Thiophen)—Benzyl | H | $CH_3$ | H |
| 17 | iPr | $CH_3$ | H | (R)—Phenyl | (S)-4-(3-Thiophen)—Benzyl | H | $CH_2OH$ | H |
| 18 | iPr | $CH_3$ | H | (R)—Thiophen | (S)-4-Phenyl—Benzyl | H | $CH_3$ | H |
| 19 | iPr | $CH_3$ | H | (R)—$CH_3$ | (S)-4-Phenyl—Benzyl | H | $CH_3$ | H |
| 20 | iPr | $CH_3$ | H | (R)—$CH_3$ | (S)-4-Phenyl—Benzyl | H | $CH_3$ | H |
| 21 | iPr | $CH_3$ | H | (R)—$CH_3$ | Cyclopentane | | $CH_3$ | H |
| 22 | iPr | $CH_3$ | H | (R)—$CH_3$ | 4(1-acetyl)piperidine | | $CH_3$ | H |

For this reason, the compound formed, which is not suitable for hydrolysis, is completely inactive with respect to said enzyme. These compounds are thus not suitable for use due to the instability thereof in preparations used in human clinical practice.

The study in solution of a compound according to the prior art was conducted as follows:

The compound according to the prior art is placed in solution in various mixtures used for parenteral administration, the solution subsequently being followed by HPLC (Kromasil C18 4.5*250 mm column, 50% CH$_3$CN (0.1% TFA)/50% H$_2$O (0.1% TFA)) to determine the composition of the solution. In any case, the formation of both products, free phosphonic acid (active compound) and the transfer product, is observed over time as illustrated in the diagram below:

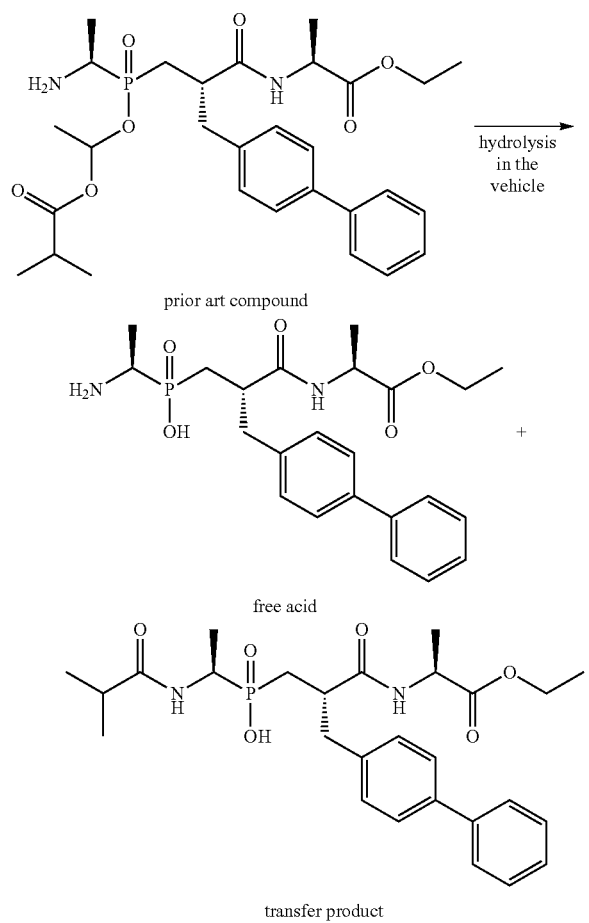

In this way, for a prior art compound solution in an ethanol/cremophor/H$_2$O mixture (1:1:8), the initial product content in the vehicle declines over time, as demonstrated in table 1 below:

|  | Time after solubilisation | | | |
| --- | --- | --- | --- | --- |
|  | 0 hrs | 3 hrs | 6 hrs | 96 hrs |
| % initial compound | 90.5% | 82.0% | 75.7% | 25.1% |

Example 25

Pharmacological Results

The molecules according to the present invention were studied for the analgesic action thereof on the most predictive animal models of the response in humans. The preferred tests are those targeting neuroinflammatory (NI) and neuropathic (NP) pain in rats and mice.

The molecules according to the present invention were found to be active on the following tests on mice:

i) pain induced by administering formalin in the paw and study of the analgesic response in the first phase considered to reflect a peripheral action on the nociceptors, and ii) hyperalgesia and allodynia induced by partial and unilateral compression of the sciatic nerve (Seltzer model) (Bennett G. J. and Xie Y. K., Pain (1998) 33, 87-107).

The techniques used in these tests are described in detail and listed in reviews such as: M. J. Millan. The induction of pain: an integrative review, in Progress in Neurobiology (1999), 52, 1-164.

The association and synergy between an opioid and gabapentin has been reported, particularly in the reference: Menendez et al (2008), Eur. J. Pharmacol, 596, 50-55.

The following tests were thus performed.

A/ Formalin Test (Phase I)

The molecules were studied at one time (90 min) for comparative tests and at two times, 90 and 150 minutes, so as to observe the period of action thereof.

Test Description:

The animals (OF1 male mice) were obtained from the Charles River breeding centre (France) and weighed 25.35 g at the start of the experiment. The weight of each mouse is taken into account for the administration of the product.

The test is based on the protocol described by S. HUNSKAAR et al., Formalin test in mice, a useful technique for evaluating mild analgesics, J. Neurosci. Methods (1995), 14, 69-75. The early part of the test (5 to 10 min after injecting formalin), is considered to reflect neuropathic pain, which is under study.

The mice (n=8) are placed individually in a transparent container (50×25 cm$^2$) and are acclimatised to this environment for 20 minutes. After this period, 20 µl of formalin (5% HCHO) in solution in physiological saline solution (H$_2$O, 0.9% NaCl) is injected subcutaneously on the plantar face of the right paw of the animal. A 26 syringe connected to a micro-syringe is used. Each mouse is then immediately returned to the test container and pain (nociceptive) responses are measured for 5 minutes (early phase). Only the number of times the paw is licked is counted.

The analgesic activity is tested after force-feeding the animals at different times (generally 20 min, 90 min and 150 min) after injecting formalin, with:

the vehicle only (ethanol, 0.5% methylcellulose in water)
the vehicle and a compound according to the invention (50 mg/kg).

The analgesic action of the product is measured by the decline in the number of times the injured paw is licked, compared to the number of times the animal receiving the vehicle only licks its paw. The total (discontinuous) licking time, expressed in seconds for each mouse, is counted for 4 min. The cumulative values for n mice are then divided by the number n of mice studied.

The results are given for the three compounds from examples 3, 4 and 8 in FIG. 1.

The three compounds exhibit powerful analgesic effects (40 to 60%) characterised by a very significant reduction in the number of licks compared to the vehicle (control) and the effects are relatively constant for the test period. In this way, an analgesic activity of the compounds according to the invention is observed at times of up to 150 min indicating the long period of action of the compounds according to the invention.

The analgesic action is blocked by pre-administering an antagonist, methyl-naloxonium, which, at the dose used (2 mg/kg), is unable to pass the blood-brain barrier (Milne R. J. et al., Neurosci. Lett. (1990), 114, 25-32), demonstrating that the activity of these molecules is performed in the peripheral region (nociceptors) where they increase the enkephalins released from the injured site. These results clearly demonstrate that the compounds according to the invention do not pass the blood-brain barrier.

B/ Comparative Study of the Analgesic Effect of the Compound from Example 8 and a Reference Molecule According to the Prior Art The reference molecule according to the prior art used for this study has the following structure:

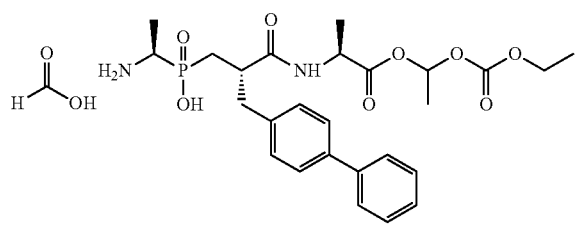 [SMILES: O=CO ; CCOC(=O)OC(C)OC(=O)[C@H](C)NC(=O)[C@H](Cc1ccc(-c2ccccc2)cc1)CP(=O)(O)[C@H](C)N]

Test A described above was repeated with the compound from example 8 (50 mg/kg; FIG. 2A) and the reference molecule according to the prior art (100 mg/kg; FIG. 2B) in order to compare the action thereof over time, 90 min after injecting formalin.

It is thus observed that the reference molecule has no activity at 90 minutes of a 100 mg/kg dose (per os) whereas, on the other hand, the compound from example 8 gives rise to a very significant analgesic activity 90 minutes at a 50 mg/kg dose (per os) which is two times lower (see FIG. 2).

The present invention is thus characterised by the development of molecules having analgesic properties by the oral route with along period of action.

C/ Anti-Allodynia and Anti-Hyperalgesia Effects of the Compound from Example 3 after Oral Administration in Mice.

This test was described in detail by A. B. Malmberg and A. I. Basbaum, Partial Sciatic nerve injury in the mouse as a model of neuropathic pain: behavioural and neuroanatomical correlates. Pain, (1998) 76, 215-222.

It was performed on OF1 male mice (Charles River, n=39), weighing 18 to 20 g, by partial ligation of the sciatic nerve on the ipsilateral side. The animals are tested over a period of 3 to 26 days after the operation.

The hyperalgesia was measured according to the method described by K. Hargreaves et al., A new sensitive method for measuring thermal nociception in cutaneous hyperalgesia, Pain (1988), 32, 77-88, using the "Plantar test" device (Bioseb, France) as the heat source. The intensity of the nociceptive stimulus is calibrated at 8-10 s with an automatic cut-off time of 20 seconds. The mean heat-induced paw withdrawal was measured on the ipsilateral (damaged nerve) and contralateral (intact nerve) paws. Each measurement is made 3 times on each paw.

The mechanical allodynia is measured as described by S. R. Chaplan et al., Quantitative assessment of tactile allodynia in the rat paw, J. Neurosci. Meth. (1994), 53, 55-63. The ipsilateral (lesion) and contralateral (control) paws are tested as above, the mechanical anti-allodynia effect being measured using the Von Frey method (Malmerg A. B. and Basbaum A. I., 1998, Pain, 76, 215-222) with filaments of increasing size likewise applying an increasing pressure.

Anti-Hyperalgesia Effect:

The results obtained, represented in FIG. 3, demonstrate that, administered orally at 50 mg/kg, the compound from example 3 gives rise to a very significant reduction (65-100%) in thermal hyperalgesia induced by a partial ligation of the sciatic nerve in the period 45-120 min with a peak effect at 90 min.

Anti-Allodynia Effect:

The effect of the compound from example 3 on mechanical allodynia is measured using the Von Frey test. The results obtained, represented in FIG. 4, demonstrate a significant long-term (45-120 min) anti-allodynia effect with a peak at 60 min equivalent to 75% of the peak response (untreated control).

D/ Potentiation of Anti-Allodynia Effects of the Compound from Example 4 by Associating with Gabapentin.

The effect of the association of the compound from example 4 and gabapentin, with both products administered orally, is measured using the Von Frey test. The results obtained, after 60 min, represented in FIG. 5, demonstrate a very high potentiation of the association (>300%) compared to the compound from example or gabapentin used alone, which prove to be inactive at the same doses. No effect is obtained on the uninjured contralateral paw.

The invention claimed is:

1. A method for treating pain comprising the administration to a patient requiring same of an effective quantity of a combination of (a) gabapentin or pregabalin and (b) at least one compound having the following general formula (I):

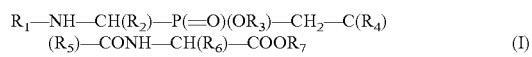

or a pharmaceutically acceptable salt thereof,
wherein:
$R_1$ represents a group —C(=O)—O—C($R^8$)($R^9$)—OC(=O)—$R^{10}$, wherein
$R^8$ and $R^9$ represent, independently of each other, a hydrogen atom or an alkyl group;
$R^{10}$ represents an alkyl group;
$R_2$ represents an alkyl group
$R_3$ represents a hydrogen atom
$R_5$ represents a hydrogen atom and $R_4$ represents:
a benzyl optionally substituted on the phenyl nucleus in para position by a phenyl group;
$R_6$ represents a linear or branched saturated or unsaturated hydrocarbon chain, comprising 1 to 6 carbon atoms; and
$R_7$ represents a radical selected from the group consisting of a hydrogen atom, a benzyl, a C2 to C4 alkyl, —CHR$^{18}$—COOR$^{19}$, —CHR$^{18}$—OC(=O)R$^{19}$ and —CHR$^{18}$—OC(=O)OR$^{19}$, wherein R$^{18}$ and R$^{19}$ represent, independently from each other, an alkyl, aryl, arylalkyl, cycloalkyl, cycloheteroalkyl, heteroalkyl, heteroaryl or heteroarylalkyl group.

2. A pharmaceutical composition comprising an effective quantity of a combination of (a) gabapentin or pregabalin and (b) at least one compound having formula (I),

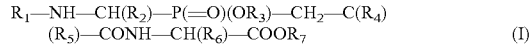

or a pharmaceutically acceptable salt thereof, and
at least one pharmaceutical acceptable vehicle, wherein:

$R_1$ represents a group —C(=O)—O—C($R^8$)($R^9$)—OC(=C)—$R^{10}$, wherein $R^8$ and $R^9$ represent, independently of each other, a hydrogen atom or an alkyl group; or $R^{10}$ represents an alkyl group;

$R_2$ represents an alkyl group:

$R_3$ represents a hydrogen atom, $R_5$ represents a hydrogen atom and R4 represents a benzyl optionally substituted on the phenyl nucleus in para position by a phenyl group;

$R_6$ represents a linear or branched saturated or unsaturated hydrocarbon chain, comprising 1 to 6 carbon atoms; and $R_7$ represents a radical selected from the group consisting of a hydrogen atom, a benzyl, a C2 to C4 alkyl, —$CHR^{18}$—$COOR^{19}$, —$CHR^{18}$—OC(=O)$R^{19}$ and —$CHR^{18}$—OC(=O)O$R^{19}$, wherein $R^{18}$ and $R^{19}$ represent, independently from each other, an alkyl, aryl, arylalkyl, cycloalkyl, cycloheteroalkyl, heteroalkyl, heteroaryl or heteroarylalkyl group.

3. The pharmaceutical composition according to claim 2, wherein the vehicle is suitable for oral administration.

4. The pharmaceutical composition according to claim 2, wherein the vehicle is suitable for administration by the oral, sublingual, parenteral, subcutaneous, pulmonary, nasal, intramuscular, intravenous, intrathecal, intra-articular or transdermal route.

5. The pharmaceutical composition according to claim 2, wherein $R_6$ represents a methyl group.

6. The pharmaceutical composition according to claim 2, wherein $R_7$ represents an hydrogen or ethyl or a benzyl or a —CH(CH$_3$)—O—C(=O)—O-Et group.

7. The method according to claim 1, wherein the pain is selected from the group consisting of sharp pain, neuropathic pain and neuroinflammatory pain.

8. The pharmaceutical composition according to claim 2, wherein the compound having formula (I) is selected from the group consisting of:

2-(2-Biphenyl-4-ylmethyl-3-{hydroxy-[1-(1-isobutyryloxy-ethoxycarbonylamino)-ethyl]-phosphinoyl}-propionylamino)-propionic acid benzyl ester, 2-(2-Biphenyl-4-ylmethyl-3-{hydroxy-[1-(1-isobutyryloxy-ethoxycarbonylamino)- ethyl]-phosphinoyl}-propionylamino)-propionic acid, 2-(2-Biphenyl-4-ylmethyl-3-{hydroxy-[1-(1isobutyryloxy-ethoxycarbonylamino)- ethyl]-phosphinoyl}-propionylamino)-propionic acid 1-ethoxycarbonyloxyethyl ester, and wherein the composition comprises gabapentin or pregabalin.

* * * * *